United States Patent
Tinjust

(10) Patent No.: US 11,179,093 B2
(45) Date of Patent: Nov. 23, 2021

(54) APPARATUS AND METHOD FOR EVALUATING COGNITIVE FUNCTION

(71) Applicant: APEXK INC., Saint-Roche-de-L'Achigan (CA)

(72) Inventor: David Tinjust, Sainte-Julie (CA)

( * ) Notice: Subject to any disclaimer, the term of this patent is extended or adjusted under 35 U.S.C. 154(b) by 0 days.

(21) Appl. No.: 16/644,006

(22) PCT Filed: Sep. 27, 2018

(86) PCT No.: PCT/CA2018/051219
§ 371 (c)(1),
(2) Date: Mar. 3, 2020

(87) PCT Pub. No.: WO2019/060995
PCT Pub. Date: Apr. 4, 2019

(65) Prior Publication Data
US 2020/0405215 A1  Dec. 31, 2020

Related U.S. Application Data

(60) Provisional application No. 62/563,699, filed on Sep. 27, 2017.

(51) Int. Cl.
*A61B 5/04*     (2006.01)
*A61B 5/00*     (2006.01)
(Continued)

(52) U.S. Cl.
CPC ........ *A61B 5/4088* (2013.01); *A61B 5/02405* (2013.01); *A61B 5/163* (2017.08);
(Continued)

(58) Field of Classification Search
CPC ....... A61B 5/4088; A61B 5/163; A61B 5/318; A61B 5/02405; A61B 5/4064;
(Continued)

(56) References Cited

U.S. PATENT DOCUMENTS 9,039,632 B2   5/2015  Kiderman et al.
10,386,645 B2 *  8/2019  Abou Shousha .... G02B 27/017
(Continued)

FOREIGN PATENT DOCUMENTS

JP      4543594 B2 *  9/2010
KR   101357800 B1 *  2/2014
(Continued)

OTHER PUBLICATIONS

Engligh-language machine translation of Korean Patent Publication KR 101357800 (Year: 2021).*
(Continued)

*Primary Examiner* — Andrey Shostak
(74) *Attorney, Agent, or Firm* — Anglehart et al.

(57) ABSTRACT

An apparatus for evaluating cognitive function of a patient. The apparatus has a physiological monitor adapted to output physiological measurements of a given bodily function of the patient, wherein the bodily function is regulated by the autonomic nervous system of the patient; a cognitive exercise evaluator adapted to obtain performance information of the patient when carrying out a cognitive exercise with a given difficulty; a general-purpose processor; and computer-readable memory adapted to store program code for evaluating the cognitive function of the patient, the program code comprising instructions to receive the physiological measurements and the performance information, and provide an evaluation of the cognitive function of the patient.

12 Claims, 13 Drawing Sheets

(51) Int. Cl.
*A61B 5/16* (2006.01)
*G16H 40/67* (2018.01)
*A61B 5/318* (2021.01)
*A61B 5/024* (2006.01)
*G02B 27/00* (2006.01)
*G02B 27/01* (2006.01)

(52) U.S. Cl.
CPC ............ *A61B 5/318* (2021.01); *A61B 5/4064* (2013.01); *A61B 5/742* (2013.01); *A61B 5/7405* (2013.01); *A61B 5/7455* (2013.01); *G02B 27/0093* (2013.01); *G02B 27/0172* (2013.01); *G16H 40/67* (2018.01)

(58) Field of Classification Search
CPC ..... A61B 5/7405; A61B 5/742; A61B 5/7455; A61B 5/16; A61B 5/024; A61B 5/08; A61B 3/113; G16H 40/67; G02B 27/0093; G02B 27/0172
See application file for complete search history.

(56) References Cited

U.S. PATENT DOCUMENTS

| | | | | |
|---|---|---|---|---|
| 2014/0200432 | A1* | 7/2014 | Banerji | A63B 21/4017 600/383 |
| 2014/0211167 | A1* | 7/2014 | Lewis | A61B 3/113 351/246 |
| 2015/0164418 | A1* | 6/2015 | Johnson | A61B 5/4884 434/236 |
| 2016/0005320 | A1* | 1/2016 | deCharms | A61B 8/0808 434/236 |
| 2016/0128892 | A1* | 5/2016 | Nimtsovitch | A61H 5/00 601/37 |
| 2016/0381534 | A1* | 12/2016 | Kwon | H04N 5/247 455/556.1 |
| 2017/0169714 | A1 | 6/2017 | Lin et al. | |
| 2017/0296421 | A1* | 10/2017 | Travers | A61H 5/00 |
| 2017/0365101 | A1* | 12/2017 | Samec | A61B 5/163 |

FOREIGN PATENT DOCUMENTS

| | | |
|---|---|---|
| WO | WO 2016/025323 A1 | 2/2016 |
| WO | WO 2018/039610 A1 | 3/2018 |

OTHER PUBLICATIONS

English-language machine translation of Japanese Patent Publication JP 4543594 (Year: 2021).*

Fechir et al., "Functional imaging of sympathetic activation during mental stress", NearoImage, vol. 50, Issue 2, Apr. 1, 2010, pp. 847-854, Available online Dec. 11, 2009 (Dec. 11, 2009), https://doi.org/10.1016/j.neuroimage.2009.12.004.

International application No. PCT/CA2018/051219 International Search Report dated Jan. 28, 2019.

International application No. PCT/CA2018/051219 Search Strategy dated Jan. 28, 2019.

International application No. PCT/CA2018/051219 Written Opinion of the Internatinoal Searching Authority dated Jan. 28, 2019.

Koenig et al., "Real-Time Closed-Loop Control of Cognitive Load in Neurological Patients During Robot-Assisted Gait Training", IEEE Transactions on Neural Systems and Rehabilitation Engineering, vol. 19, No. 4, Aug. 2011 (Aug. 2011), pp. 453-464 DOI: 10.1109/TNSRE. 2011.2160460.

Reiner et al., "Estimating mental Workload through event-related fluctuations of pupil area during a task in a virtual World", International Journal of Psychophysiology, Jul. 2014; 93(1):38-44. Available online Dec. 1, 2013 (Dec. 1, 2013), PMID: 24291237.

* cited by examiner

APPARATUS AND METHOD FOR EVALUATING COGNITIVE FUNCTION

The present patent application is a 371 of International PCT patent application No. PCT/CA2018/051219, with a filing date of Sep. 27, 2018, that claims priority of the U.S. provisional patent application No. 62/563,699 filed on Sep. 27, 2017.

TECHNICAL FIELD

The present application relates to the field of cognitive function testing.

BACKGROUND

Evaluation of cognitive function of a patient may be used to determine the degree of cognitive impairment resulting from a disease, accident, disorder, etc. Cognitive function evaluation is also useful to determine if a patient's cognitive function is improving, such as when the patient is recovering cognitive function following an accident.

The evaluation of cognitive function involves making the user perform certain tests tailored for the purposes of the evaluation. These tests may include, for example, eye tracking exercises, such as when the patient's peripheral vision is evaluated. However, the accuracy of these tests leave room for improvement, especially when a more accurate test would allow for the identifying of minor brain injuries (e.g. mild concussions) suffered by patients, such as, for example, athletes. These mild brain injuries may lead to more serious conditions if left undetected/untreated. The current state of the art does not provide for an accurate and reliable mechanism for detecting/evaluating these minor brain injuries or diseases. Moreover, a more accurate test, that would enable a medical practitioner to better evaluate the rate of recovery of a patient, may allow the practitioner to better tailor treatment for the patient's condition. Finally, a more accurate evaluation would insure that the cognitive or visual-cognitive exercises that are being assigned to the patient are not negatively jeopardizing the patient's recovery, such as by overstressing the patient's brain by performing too challenging exercises.

Applicant has found that certain vision tests that measure the fitness of the visual cortex and/or of the eyes/oculomotricity are useful in the field of visual cognitive testing and more specifically to the field of evaluation of concussions and cognitive performance, the latter including athletic performance training and evaluation.

Examples of vision testing include:

The cover test—a test that involves observing how the eye moves when it is covered for a few seconds and then uncovered;

Punctum proximum—a test that involves having the subject focus on an object, such as the tip of a pencil, at a distance of about 60 cm and then observing the eyes of the subject as the object is moved towards the subject's nose until the eyes of the subject can no longer focus on the object;

Sagittalisation—a stereovision test that involves viewing separate images with each eye, allowing the subject to see fused or separate objects, possibly with different depths, as a function of stereovision abilities.

The prism test—a prism test involves placing a prism in front of one eye while the subject views an object, typically at a distance. The prism strength is changed to determine the subject's ability to maintain binocular vision of the object under the effect of the prism in front of the one eye.

Such tests are performed by, for example, an eye doctor or a binocular vision specialist, using simple tools in interaction with the subject. The results of the tests are more qualitative in nature as an exact measurement is difficult for the eye doctor to perform.

Moreover, the current state of the art in the evaluation of cognitive function lacks this additional accuracy. A more accurate mechanism to evaluate cognitive function would therefore be advantageous in order to improve cognitive function testing, treatment and recovery.

SUMMARY

Applicant has found that an apparatus for providing an improved cognitive evaluation of a patient may be achieved by obtaining responsiveness information of the patient when conducting the cognitive exercise. The responsiveness of the patient may be, for example, the eye movement of the patient, the responsiveness of the autonomic nervous system of the patient (physiological information), the biomechanical/muscular information of the patient, and/or the brain activity of the patient. Moreover, the apparatus may monitor this responsiveness, and compare the observed responsiveness with the expected responsiveness. The apparatus may then adapt the generated cognitive exercise for the patient as a function of the comparison information. For instance, if the expected responsiveness data corresponds to the observed responsiveness data of the patient when conducting the test, then this may be an indication that, for instance, the patient is capable of carrying out effectively the cognitive exercise, and, e.g., the difficulty of the cognitive exercise may be increased (i.e. an adaptation of the cognitive exercise). Conversely, if, for example, the observed responsiveness data does not correspond to the expected responsiveness data, then this may be an indication that the patient is having difficulty performing the cognitive exercise, and, for instance, the difficulty of the cognitive exercise may be lowered.

The apparatus may also be connected to a remote medical practitioner who can remotely send information and/or commands to adapt the cognitive exercise generated for the patient. Similarly, the medical practitioner may receive responsiveness data, performance data, cognitive evaluation, etc., from the apparatus, in order to provide a diagnosis of the patient, or to further monitor the patient remotely. The medical practitioner may also remotely transmit a diagnosis or information to the patient via the apparatus. The apparatus may also remotely transmit a diagnosis or information to the patient via the apparatus.

The physiological measurements may also provide an indication of if the state of the autonomic nervous system can impact upon the cognitive function of the patient, or recovery of the patient's cognitive function.

Furthermore, applicant has also discovered that an apparatus and/or method for assessing cognitive function of a person may be improved by adding a component or step for assessing the autonomic nervous system response (ANS), a physiological response, before, during and/or after the evaluation of cognitive function. Similarly, a physiological response may also have an impact upon cognitive function, or recovery of cognitive function when a patient's cognitive function is impaired (e.g. as a result of injury). This additional monitoring provides for a more accurate evaluation, allowed for more sensitive and effective treatment, and detection of minor brain injuries, conditions and/or disorders.

More specifically, applicant has discovered that the autonomic nervous system of a person responds to the degree of stress and/or exertion experienced by the brain when performing specific cognitive tasks. A patient suffering from a brain disorder may display changes in measurements of different bodily functions regulated by the ANS that are akin to that patient performing, for example, physical exercise (e.g. increased respiratory rate, increase heart rate, temperature, dilated pupils, etc.) when conducting a cognitive exercise.

Visual mechanisms can also be affected by an overload of the autonomic nervous system.

For instance, the heart rate of the patient may increase as a result of the difficulty of the cognitive exercise and/or the strain put on the brain as it attempts to carry out the cognitive exercise. As a result, by monitoring certain bodily functions regulated by the autonomic nervous system, it is possible to improve the accuracy of detecting the first signs of cognitive stress resulting from cognitive tasks. This increased accuracy may act as a confirmation of the test results obtained from the performance of the cognitive exercise, or as a mechanism to identify cognitive difficulties even before such difficulties become apparent from the test results resulting from the patient carrying out the cognitive exercise. Therefore, the present application relates to an improved apparatus and/or method to assess and monitor the cognitive function of the person, the apparatus and/or method sensitive to changes in bodily functions tied to the autonomic nervous system such as a change in the pulse/heart rate of the person subject to the testing.

Moreover, the use of a head-mounted display having an eye-gaze detector can be used to detect a difference in eye-gaze direction between the two eyes that results from pairs of vision test images being displayed.

A first broad aspect is an apparatus for evaluating cognitive function of a subject. The apparatus includes a physiological monitor adapted to output physiological measurements of a given bodily function of the subject, wherein the bodily function is regulated by the autonomic nervous system of the subject. The apparatus includes a cognitive exercise evaluator adapted to obtain performance information of the subject when carrying out a cognitive exercise with a given difficulty. The apparatus includes a general-purpose processor. The apparatus includes computer-readable memory adapted to store program code for evaluating the cognitive function of the subject, the program code comprising instructions to receive the physiological measurements and the performance information, and provide an evaluation of the cognitive function of the subject as a function of the performance level of the subject in carrying out the cognitive exercise, determined from the performance information and as a function of the parameters of the cognitive exercise, the physiological measurements, wherein the physiological measurements provide an indication of a presence or an absence of cognitive exertion, and/or the difficulty of the cognitive exercise.

In some embodiments, the physiological monitor may be a heart rate monitor. In some embodiments, the physiological monitor may be an electrocardiograph.

In some embodiments, the cognitive exercise evaluator may include an eye-tracker.

In some embodiments, the eye-tracker may be included in a head mounted display.

In some embodiments, the apparatus may include a supervisor input interface adapted to allow a supervisor evaluating the cognitive function of the subject to control parameters of the cognitive exercise.

In some embodiments, the apparatus may include an input interface adapted to receive feedback input from the subject regarding the subject's experienced cognitive fatigue.

In some embodiments, the apparatus may include an input interface adapted to receive feedback input from the subject regarding the subject's experienced cognitive state (e.g. which may include cognitive fatigue).

In some embodiments, the apparatus may include an additional physiological monitor for measuring an additional bodily function and outputting additional physiological measurements, wherein the additional bodily function is regulated by the autonomic nervous system of the subject.

In some embodiments, the apparatus may include a transceiver for establishing a connection with a remote computer, wherein the transceiver transmits data regarding the subject's cognitive function via the connection. In some embodiments, the connection may be wired. In some embodiments, the connection may be wireless.

In some embodiments, the apparatus may include a display.

In some embodiments, the apparatus may include a biomechanics muscular inertial monitor/sensors adapted to output biomechanics muscular inertial measurements of a given biomechanical muscular movement of the subject. The providing an evaluation of the cognitive function of the subject may be as a function of the performance level of the subject in carrying out the cognitive exercise, determined from the performance information and as a function of the parameters of the cognitive exercise, the physiological measurements, wherein the physiological measurements provide an indication of a presence or an absence of cognitive exertion, the biomechanics muscular measurements and/or the difficulty of the cognitive exercise.

In some embodiments, the apparatus may include a brain activity monitor adapted to output brain activity measurements of given brain activity of the subject. The providing an evaluation of the cognitive function of the subject may be as a function of the performance level of the subject in carrying out the cognitive exercise, determined from the performance information and as a function of the parameters of the cognitive exercise, the physiological measurements, wherein the physiological measurements provide an indication of a presence or an absence of cognitive exertion, the biomechanics muscular inertial measurements, the brain activity measurements and/or the difficulty of the cognitive exercise.

A second broad aspect is a method of assessing and/or measuring cognitive exertion of a subject. The method includes measuring a bodily function of the subject to produce physiological measurements during or after the performance of a cognitive task by the subject, wherein the bodily function is regulated by the autonomic nervous system of the subject, and assessing the physiological measurements for the presence or absence of cognitive exertion by comparing the physiological measurements with a reference value corresponding to the bodily function.

In some embodiments, the cognitive task may be a cognitive exercise of a given difficulty adapted to measure the cognitive function of the patient, and wherein the method may include measuring the performance level the subject (and generating performance data therefrom) when performing the cognitive exercise; correlating the measured performance level with the assessed physiological measurements;

and evaluating the cognitive function of the subject in accordance with the correlation between the measured performance level and the assessed physiological measurements, and as a function of the difficulty of the cognitive exercise.

In some embodiments, the evaluating the performance level of the subject in performing the cognitive exercise may include tracking the eye movement of the subject when performing the cognitive exercise.

In some embodiments, the method may include modulating the difficulty of the cognitive exercise as a function of the assessed presence or absence of cognitive exertion.

In some embodiments, the method may include re-evaluating the performance level of the subject when performing the cognitive exercise following the modulation of the difficulty of the cognitive exercise.

In some embodiments, the cognitive task may be a task that the subject performs in the work environment of the subject.

In some embodiments, the cognitive task may be a task that the subject performs in the home environment of the subject.

In some embodiments, the measuring of the bodily function may include measuring the heart rate and derivative data from heart rate of the subject.

In some embodiments, the providing an evaluation of the cognitive function may include comparing the measured heart and derivative data from heart rate with a resting heart rate of the subject.

In some embodiments, the method may include signaling the subject when the cognitive exertion of the subject is assessed to be present and to be above a given threshold.

In some embodiments, the method may include prompting the subject to provide feedback regarding the subject's cognitive fatigue during or after performing the cognitive task.

In some embodiments, the method may include providing a recommended time that the subject should perform the cognitive task as a function of the assessed presence or absence of cognitive exertion.

A third broad aspect is a vision testing apparatus. The apparatus includes a head-mounted display for providing separate images to each eye; an eye gaze detector for determining a direction of gaze of each eye; an image display controller for displaying left eye and right eye images having predetermined properties; and a test controller for analysing the direction of gaze of each eye as a function of the predetermined properties of the left eye and right eye images to determine a vision test result.

In some embodiments, the test controller may be responsive to a difference in a direction of gaze between the eyes as a result in a change in the left eye and right eye images.

In some embodiments, the test controller may be responsive to both eyes having a gaze direction corresponding to a selection of one of a plurality of objects within the left eye and right eye images.

A fourth broad aspect is an adaptive apparatus for evaluating cognitive function of a patient. The apparatus includes a stimulus output interface configured to output stimulus perceivable by the patient associated with a given cognitive exercise; a response evaluator adapted to collect observed responsiveness data on the responsiveness of the patient when conducting the given cognitive exercise; memory configured to store cognitive exercise information and expected responsiveness data. The apparatus also includes a controller configured to generate a generic cognitive exercise as a function of the cognitive exercise information; receive the observed responsiveness data from the response evaluator; obtain the expected responsiveness data retrievable from the memory; compare the observed responsiveness data to the expected responsiveness data, and output comparison data as a function of the comparison; generate an adapted cognitive exercise as a function of at least the cognitive exercise information and the comparison data; and generate a cognitive evaluation of the patient. The given cognitive exercise is the generic cognitive exercise or the adapted cognitive exercise. The given cognitive exercise may be, during one instance when the patient is performing the cognitive exercise, a generic exercise (e.g. produced by the apparatus without regard to responsiveness of the patient and the comparison data), and then, in further instances, an adapted cognitive exercise, adapted based on at least the comparison data generated, for instance, based on prior tests.

In some embodiments, the apparatus may further include a transceiver in communication with a remote computer of a remote medical practitioner, the controller may be further configured to generate the adapted cognitive exercise further in accordance with remote medical practitioner input information generated from a medical practitioner monitoring the patient remotely received via the transceiver.

In some embodiments, the stimulus generator may include a head-mounted display or a hologram display. In some embodiments, the head-mounted display or hologram display may generate virtual reality, augmented reality and/or a mixed reality experience.

In some embodiments, the head-mounted display may include a vision tracker, and the response evaluator may include the vision tracker to generate the observed responsiveness data as a function of observed eye movement of the patient when conducting the given cognitive exercise.

In some embodiments, the stimulus generator may have a haptic display.

In some embodiments, the stimulus generator may include a speaker to generate an auditory stimulus.

In some embodiments, the response evaluator may include a physiological monitor adapted to output as the observed responsiveness data physiological measurements of a given bodily function of the patient, wherein the bodily function may be regulated by the autonomic nervous system of the patient. In some embodiments, the physiological monitor may be a heart-rate monitor.

In some embodiments, the response evaluator may include a biomechanics evaluator adapted to output as the observed responsiveness data biomechanics data corresponding to muscle movement or muscle activity of the patient when performing the given cognitive exercise.

In some embodiments, the response evaluator may include a brain activity evaluator adapted to output as the observed responsiveness data brain activity data of the patient.

In some embodiments, the apparatus may include a patient input interface adapted to receive information entered by the patient before, during or after performing the given cognitive exercise.

In some embodiments, the patient input interface may be a touchscreen, a microphone, a keyboard, and/or a mouse.

A method of assessing exertion of a patient that can deleteriously affect cognitive recovery of the patient having suffered cognitive function impairment. The method includes measuring a bodily function of the patient to produce physiological measurements during or after an activity performed by the patient, wherein the bodily function is regulated by the autonomic nervous system of the patient; comparing the physiological measurements with a tolerance level for the bodily function that is set in order to delimit when exertion of the patient may impact recovery of the patient whose cognitive function is impaired; and alerting the patient if the physiological measurements are outside of the tolerable range.

In some embodiments, the method may include monitoring physiological measurements remotely, wherein the alerting may be triggered an alert sent by a medical practitioner performing the remote monitoring.

In some embodiments, the activity may be a cognitive exercise.

In some embodiments, the activity may be a physical activity.

In some embodiments, the bodily function may be the heartbeat of the patient and the physiological measurements may correspond to the heart rate variability of the patient.

BRIEF DESCRIPTION OF THE DRAWINGS

The invention will be better understood by way of the following detailed description of embodiments of the invention with reference to the appended drawings, in which.

DETAILED DESCRIPTION

Figure 1:
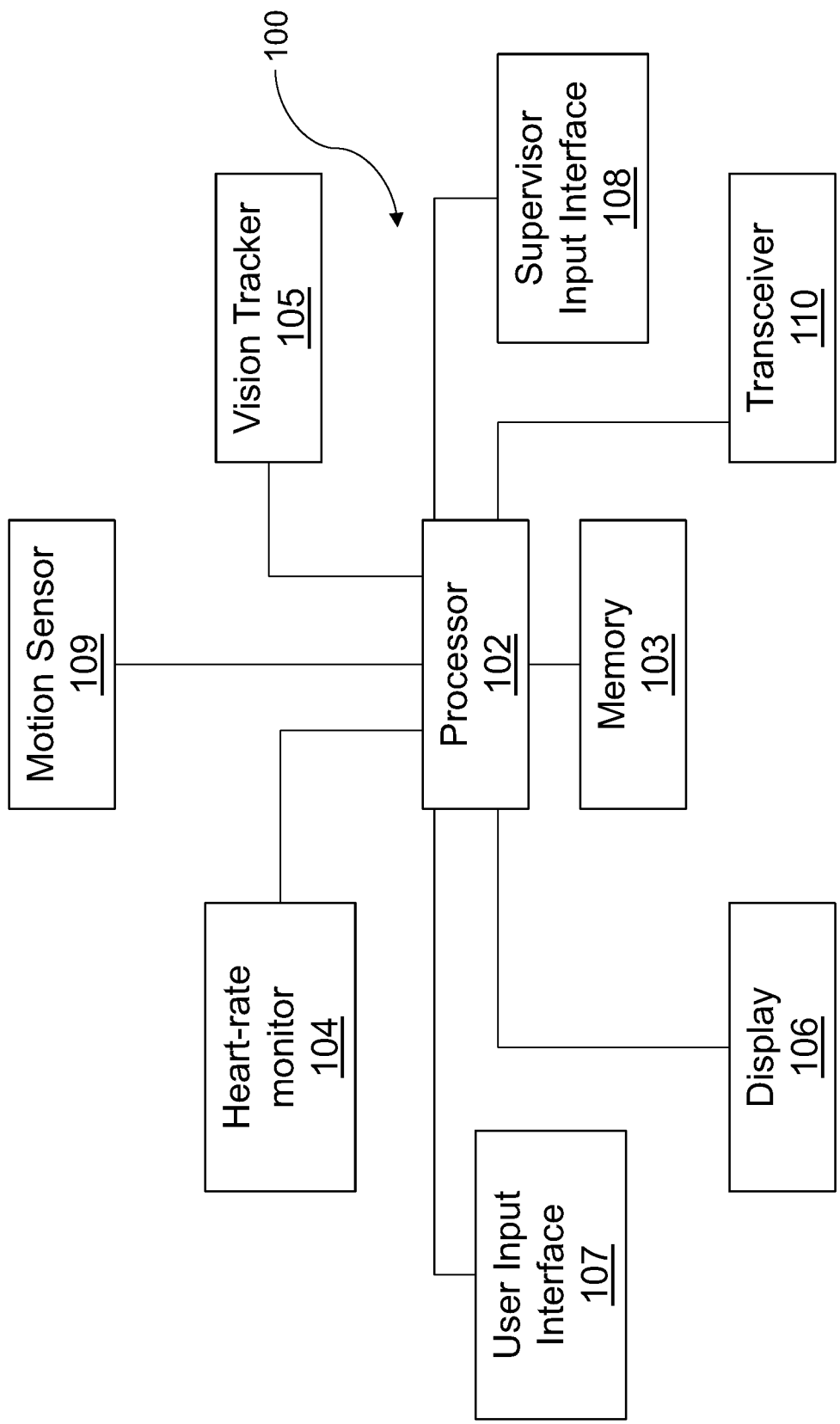
FIG. 1 is a block diagram of an exemplary apparatus for evaluating cognitive function by measuring changes of the autonomic nervous system.

The present application relates to an improved method and device for evaluating the cognitive function of a person.

The device incorporates the using of response evaluation, such as vision tracking, monitoring physiological changes, monitoring muscular biomechanics and/or monitoring brain activity as described herein. The responsiveness data of the patient collected when the patient is performing the cognitive exercise is compared with expected responsiveness data for the given cognitive exercise. The comparison allows the apparatus to adapt the exercises provided to the patient so that the cognitive exercise is, for instance, better suited and tailored to evaluate more accurately the health of the patient.

For instance, the device may monitor physiological changes of the patient by measuring changes in bodily functions regulated by their autonomic nervous system. As the cognitive exercise performed by the person results in increased mental strain, or if the mental exercise is arduous or overtaxing for the person, then an autonomic nervous system response can be detected and measured to improve the evaluation of the person's cognitive state. For example, in the cases of patients having suffered from a concussion, obtaining information regarding their autonomic nervous system response may be helpful in adjusting the difficulty of the exercise in order to not overtax the brain. A patient recovering from a concussion may be sensitive to the difficulty of certain mental exercises, where an overly-challenging exercise may even set the patient back in the patient's recovery. Therefore, a mechanism for rapidly identifying such cognitive overtaxing and adjusting in response the difficulty, nature of parameters of the cognitive exercise may be helpful, for instance, in the clinical setting, where the medical practitioner can receive data, provided by the autonomic nervous system of the patient, so as to adjust the level of the exercise in consequence. The assessment of these bodily function measurements may also provide increased accuracy in cases of mild traumatic brain injury, disease or disorders resulting in subtler cognitive impairment. Similarly, such a device may also be used by a patient recovering from a cognitive-impairing disorder or injury who is starting to get back into his or her daily routine (e.g. going back to work). The patient may use, for example, the cognitive evaluation apparatus at the office, where the apparatus can inform the patient, by evaluating its ANS response, if the cognitive task that the patient is carrying out at work is overtaxing the brain. The apparatus can then signal the patient to the change in its ANS level, and warn the patient that it is warranted to cease the overtaxing cognitive task, to not risk delaying recovery. For instance, the patient may be an accountant, who had suffered from a concussion, who is auditing a company. As the accountant is sifting through the numbers for the audit, his apparatus warns him that his heart rate is increasing over a recommended threshold. The apparatus may then provide a warning signal to stop the activity. The accountant may stop carrying out the auditing exercise to not deleteriously affect his recovery.

Definitions

In the present application, by "autonomic nervous system" or "ANS" it is meant a control system of the body that acts largely unconsciously and regulates bodily functions such as the heart rate, digestion, respiratory rate, pupillary response, urination, etc. It is tied to the fight-or-flight response. Therefore, when measuring changes or functions to the autonomic nervous system, also defined herein as measuring physiological changes, such may include measuring such bodily functions as heart rate (or changes thereof), pupil dilation (or changes thereof), respiratory rate (or changes thereof), perspiration, or any other bodily function regulated by the ANS.

An exemplary change to the bodily function that may be measured and used to provide information on cognitive function, or exertion that could deleteriously impact cognitive function, is measuring the cardiovascular variability or heart rate variability of a patient (e.g. by using an electrocardiograph). An analysis of the heart rate variability, and an analysis for instance of the standard deviation of NN intervals, may provide information on the status and/or condition of the autonomic nervous system of the patient, which may further provide an indication of the patient's cognitive health (e.g. improving a cognitive evaluation of the patient), or to detect if the state of the autonomic nervous system may impact upon the cognitive health or cognitive function of the patient.

By "difficulty" of a cognitive exercise, it refers to a measure of the challenge imposed on the mind by the performance level required to complete the given cognitive exercise, where, e.g., a more difficult exercise may require a greater cognitive load (a greater total amount of mental effort). For example, difficulty levels of cognitive exercises may be classified as "easy", "moderate" and "hard".

By "exercise parameters" it is meant the conditions, settings, rules, etc. of the cognitive exercise.

By "biomechanical muscular", it is meant the muscle movement or muscular activity of a patient, such as when the patient is to carry out a cognitive task that requires physical movement carried out by the patient's musculature (e.g. movement of the legs, of the arms, tilting of the head, etc.)

By "brain activity", it is meant activity carried out by the central nervous system.

Apparatus for Cognitive Function Evaluation:

Reference is now made to FIG. 1 illustrating an exemplary apparatus for cognitive function evaluation 100. Apparatus 100 has a processor 102, memory 103 and a physiological function measurement device 104 (in FIG. 1, as an example, the physiological measurement device is shown as a heart rate monitor). The apparatus 100 may have a cognitive exercise evaluator 105 (in FIG. 1, as an example, the cognitive exercise evaluator is shown as a vision tracker). The apparatus 100 may also have a display 106 and/or a user input interface 107, where the user is a person whose cognitive function is being evaluated. The apparatus 100 may also have a supervisor input interface 108, where the supervisor is the person/entity (e.g. medical practitioner) who is responsible for evaluating the cognitive level of the person. The apparatus 100 may also have a transceiver 110 for transmitting and/or receiving data regarding the cognitive level evaluated and/or the physiological measurements to and/or from a remote location or a device and/or display other than the apparatus 100. The apparatus 100 may also have a motion sensor 109.

The processor 102 is a general-purpose programmable processor. In this example, the processor 102 is shown as being unitary, but the processor may also be multicore, or distributed (e.g. a multi-processor). The processor 102 may be a micro-processor.

The memory 103 stores program instructions and data used by the processor 102. The computer readable memory 103, though shown as unitary for simplicity in the present example, may comprise multiple memory modules and/or cashing. In particular, it may comprise several layers of memory such as a hard drive, external drive (e.g. SD card storage) or the like and a faster and smaller RAM module. The RAM module may store data and/or program code currently being, recently being or soon to be processed by the processor 102 as well as cache data and/or program code from a hard drive. A hard drive may store program code and be accessed to retrieve such code for execution by the processor 102, and may be accessed by the processor 102 to store, for instance, cognitive evaluating data, physiological measurements, correlation between cognitive evaluation data and physiological measurements, etc., as explained herein. The memory 103 may have a recycling architecture for storing, for instance, cognitive evaluation data, physiological measurements, correlation between cognitive evaluation data and physiological measurements, where older data files are deleted when the memory 103 is full or near being full, or after the older data files have been stored in memory 103 for a certain time. In some examples, the memory 103 may also be or include remote storage (e.g. Cloud storage). The processor 102 and the memory 103 may be connected, for instance, via a BUS.

The physiological measurement device 104 is a device to measure a bodily function controlled by the ANS of the person. The physiological measurement device 104 measures the bodily function and transmits the bodily function measurements to the processor 102 that may store the physiological measurements in memory 103 or assess the measurements as explained herein. The physiological measurement device 104 may be, for example, a heart rate monitor as is known in the art (in some examples, this may be performed using equipment similar to those used with an electrocardiograph, using leads and electrodes, where the electrodes may be placed on the part of the chest in proximity to the heart to obtain accurate reads of the heart rate; in other examples, the heart rate monitor may be for example, a watch that reads a person's heart rate, or any other device to obtain an accurate reading of the heart rate of a person) to monitor the heart rate of a person. In some examples, the physiological measurement device 104 may be a respiratory monitor to monitor the respiratory rate of the patient; a mechanism for measuring changes in pupil dilation, a perspiration monitor, etc.

The cognitive exercise evaluator 105 is a device for obtaining readings from a person that are used to evaluate the cognitive function of a person as a result of the person's performance of an exercise. The cognitive exercise evaluator 105 generates performance data as a function of the input received from the patient when performing the cognitive exercise. This input may include actions controlled and deliberate action by the patient who is trying to perform the cognitive exercise (e.g. pressing a button when a response is given; moving an arm or a leg to a response; producing sound as a response; squeezing a handle in response; etc.). For instance, the person may be subject to a cognitive exercise where he or she is to identify objects on a screen. In this example, the cognitive exercise evaluator 105 may be a vision tracker (monitoring the person's eye movement), where the eye movement is tracked to obtain information on if the person is viewing the objects that are appearing on the screen and is capable of performing the required exercises. In some examples, the vision tracker may be present in a head mounted display used by the patient. However, it will be understood that other devices for measuring cognitive function may be used as a cognitive exercise evaluator 105. For instance, the cognitive exercise evaluator may be a touch screen, where the patient is to touch the screen in response to the game, and the touch screen, in combination with the program code executed by the processor 102, identifies what has been correctly touched by the patient and evaluates exercise performance level as a function of the exercise parameters and the input received on the touch screen. In other examples, the cognitive exercise evaluator 105 may be a keypad (where certain keys are to be processed at a designated time as a function of the exercise parameters), a movement sensor (e.g. the patient is to move a right or left arm as a function of the exercise parameters), etc. It will be understood that in some examples, where the apparatus 100 is used to measure the cognitive exertion of a person, the apparatus may not have a cognitive exercise evaluator 105.

The apparatus 100 may have a user input interface 107 for the user to provide input to apparatus 100 or the supervisor in order to change the function of the apparatus 100. The input may be, for example, an option to allow the user to personally select to increase or lower the difficulty of the cognitive exercise, stop the cognitive exercise, inform the supervisor to stop the cognitive exercise, start the cognitive exercise and/or change the difficulty of the cognitive exercise. The user input interface 107 may also have an input so that the user may store in memory the current cognitive exercise results, or retrieve from memory for comparison prior exercise results. It will be understood that the user input interface 107 may provide the user (e.g. the patient or the person whose cognitive function is being evaluated) with other options to interact with the apparatus 100 and/or the supervisor without departing from the present teachings.

The supervisor input interface 108 is used by the supervisor (e.g. the medical practitioner who is evaluating the cognitive function) to provide input into the apparatus 100, such as, start and/or stop the cognitive exercise, increase or lower the difficulty of the cognitive exercise, store certain exercise parameters, physiological measurements, cognitive performance results, etc., into memory, etc. The supervisor input interface 108 allows the supervisor to provide input to control the apparatus 100. The supervisor input interface 108 may be at a remote location from the user input interface 107 or the physiological monitor 104. The supervisor can provide input to the user from the remote location, such as by sharing remotely a diagnosis with the patient. In some examples, where the apparatus comprises an intelligence module as described herein, the apparatus can also provide input (e.g. appearing on an external screen; a message sent to the computer, smartphone, or smartwatch of the patient) directly to the patient via its intelligence module.

The motion sensor 109 may be used as a cognitive exercise evaluator to obtain information regarding the subject's responsiveness to a cognitive exercise. For instance, when the cognitive exercise requires that the user responds by moving a part of his or her body, such as by lifting a right or left arm, or moving the right of left leg, the motion sensor 109 may pick up on these movements and send the motion detection data to the processor 102. The processor 102 may use the motion data to evaluate the performance level of the subject in carrying out the cognitive exercise. In some examples, a motion sensor may be a passive infrared sensor, a microwave sensor, an ultrasonic sensor, photodetectors, accelerometers, gyroscopes, and infrared lighting elements combined with machine learning algorithms as are known in the art to detect gestures and motions, etc.

The apparatus 100 may also have one or more displays 106. The display 106 may allow the person who is being evaluated to, e.g., carry out the cognitive exercise (e.g. the exercise or game appears on screen), view the cognitive performance results and/or Physiological measurements. The display 106 may, e.g., provide the supervisor with a graphic user interface, display the cognitive performance results and/or Physiological measurements to the supervisor, etc. For instance, the display 106 may be a head-mounted display (present in a headset), where the head mounted display may have vision tracking capabilities. The vision tracking capabilities allows the monitoring of the gaze and/or eye movement of the patient, and where a software-based module receives the measured eye movement data and compares the measured gaze and/or eye movement data with expected eye movement data of, for instance, a healthy patient, when performing a given cognitive task.

The transceiver 110 may establish a connection, either wired or wireless, with a remote computer, remote user, external memory, to transmit data over the connection thereto. The data may be related to the cognitive performance results, the cognitive evaluation, the physiological measurements, etc. The transceiver 110 may also receive via the wired and/or wireless connection data cognitive performance results, the correlation(s) between the cognitive evaluation and the physiological measurements, new cognitive exercises, cognitive exercise parameters, etc. The wireless connection may use a wireless protocol such as 802.11, WLAN, WPA, WEP, Wi-Fi, wireless broadband, etc. The wireless connection may also be a short-range wireless connection such as one using a Bluetooth protocol. As such, the transceiver 110 may transmit the recorded data to, for instance, a physician located remotely. The physician may monitor remotely the data regarding the patient. The physician (or, in some examples, the intelligence module) may also be alerted to data that is indicative of the patient suffering from cognitive fatigue, allowing the physician to, for instance, by using the supervisor input interface 108, provide an alert back to the patient indicative of cognitive overexertion. The physician may also provide the patient with a diagnosis remotely.

Therefore, the apparatus 100 measures, for instance a bodily function regulated by the ANS, or changes thereto over time, and uses these measurements to assess when the person is starting to undergo cognitive exertion as a function of the readings or change in the measured bodily function. For instance, as the patient's cognitive exertion increases, so does one of the bodily measurements change, the changes associated with increased exertion. For instance, if pupil dilation is being measured, the patient's pupils may dilate more as the patient performs a difficult cognitive exercise. The apparatus 100 may observe these changes, and compute these changes to evaluate the cognitive function of the patient, evaluate the effectivity of a given cognitive exercise, evaluate the cognitive strain exertion by the patient etc. In some examples, the apparatus 100 may then react in real-time to the physiological measurements, such as by lowering/increasing the difficulty of the cognitive exercise, or providing a warning signal to the user to stop performing an exercise that is causing undesirable cognitive strain. The warning signal may be modulated as a function of the physiological measurement (e.g. a measurement indicative of a high strain may result in the apparatus 100 outputting a signal to stop the activity immediately, where a measurement indicative of a low strain may result in the apparatus 100 outputting a signal recommending the user to watch out or slow down whatever he/she is doing).

In some examples, more than one different physiological measurement may be taken. For instance, both the patient's heart rate and respiratory rate may be monitored.

Figure 2:
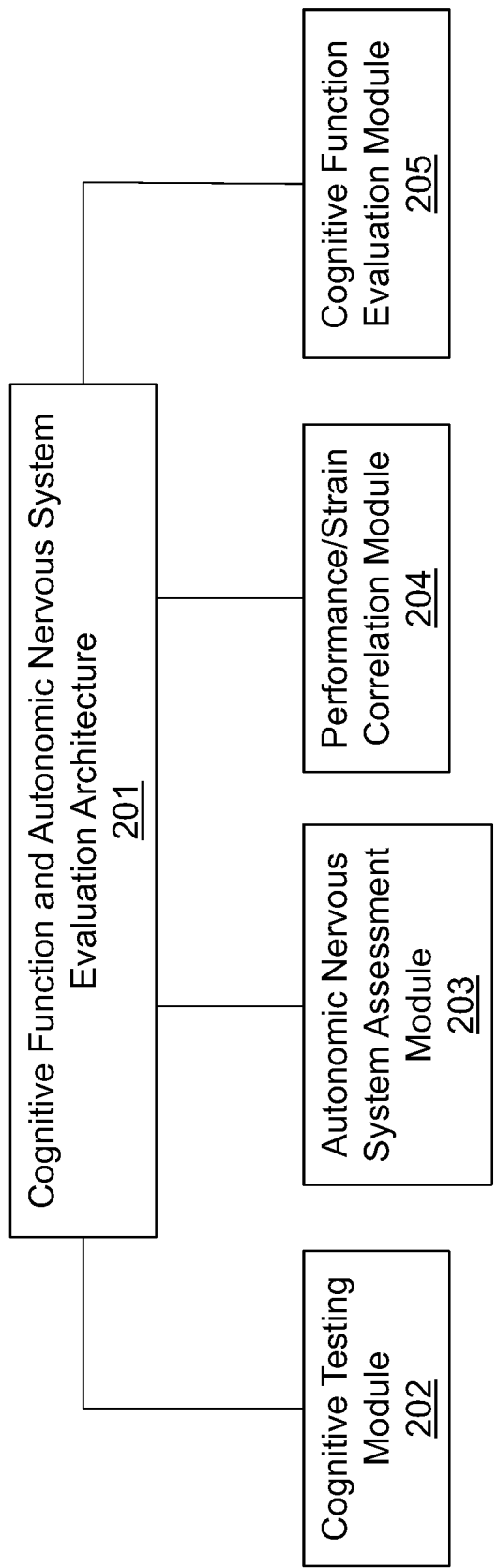
FIG. 2 is a block diagram of exemplary program code architecture, stored in memory of an exemplary cognitive function evaluation apparatus, for evaluating the cognitive function of a person.

Cognitive Function Evaluation Architecture:

Reference is now made to FIG. 2, illustrating exemplary modular architecture of exemplary program code that can be stored in memory (a storage medium) and executable by a processor of an apparatus 100 to evaluate the cognitive function of a person using physiological measurements that are regulated by the ANS.

Cognitive function and autonomic nervous system evaluation architecture 201 is program code that can be carried out by the processor 102 to evaluate the cognitive function of a person.

The architecture 201 may have a cognitive testing module 202. The architecture 201 may have an autonomic nervous system assessment module 203, a performance/strain assessment module 204 and a cognitive function evaluation module 205.

The cognitive testing module 202 is program code stored in memory and executable by a processor to test the cognitive function of a person in response to a cognitive exercise. The cognitive testing module 202 may have a set of instructions to carry out a given cognitive exercise or game when processed.

The cognitive testing module 202 then measures the responsiveness of a person to the cognitive exercise, and may store the results and/or measurements in memory. The cognitive testing module 202 may run in parallel with the ANS assessment module 203. The cognitive testing module 203, when the cognitive exercise is assessed as being complete, may call up the performance/strain correlation module 204. In some examples, the performance/strain correlation module 204 may be called by the ANS assessment module 203. In some examples, the cognitive testing module 202 may also call the ANS assessment module 203 once the cognitive testing module 202 is started.

In some examples, the cognitive testing module 202 may store in memory the cognitive exercise result data with time stamps of when the cognitive exercise result data was taken. The cognitive testing module 202 may assess cognitive performance level as a function of time by assessing changes in the cognitive exercise results. In some examples, the time stamps may be stored as metadata of the cognitive exercise result data. In some examples, the cognitive testing module 202 may transmit to the performance/strain correlation module 204 the cognitive exercise result data with time stamps of when the cognitive exercise result data was taken.

In some examples, where the cognitive function of the patient is not being directly evaluated, the architecture 201 may not have a cognitive testing module 202. This may be the case, for example, in some embodiments of an apparatus 100 that is used to measure increased cognitive strain of a recovering subject in order to not delay the subject's recovery. In these examples, the cognitive exercises performed by the subject are those of regular day-to-day activity, such as though demanded by a job.

The ANS assessment module 203 is program code stored in memory and executable by the processor to receive data transmitted from the physiological measurement device 104 relating to ANS bodily function measurements of the patient and process the physiological measurement device to assess changes in the physiological measurements of the patient. For instance, in some examples where the physiological measurements are related to the heart rate of the patient, the ANS assessment module 203 receives the heart rate data from the patient and processes the data to measure changes in the heart rate by comparing the current heart rate with, for example, a resting heart rate to calculate the difference. In some embodiments, the ANS assessment module 203 may further have computer-readable instructions to compare the physiological measurements, change of physiological measurements, or the calculated difference in physiological measurements with a reference value, with a suitable value indicative of cognitive exertion. The ANS assessment module 203 may then output a value indicative of cognitive exertion, the absence cognitive exertion, or the degree of cognitive exertion, depending upon the compared physiological measurements. In other embodiments, the ANS comparison may be performed, for example, by the performance/strain correlation module 204. The ANS assessment module 203 may store in memory the physiological measurements with time stamps corresponding to when the physiological measurements where taken. In some examples, the time stamps may be stored as metadata of the physiological measurements. In some examples, ANS assessment module 203 may transmit to the performance/strain correlation module 204 the physiological measurements with time stamps corresponding to when the physiological measurements where taken.

In the examples where the cognitive testing module 202 does not call the performance/strain correlation module 204, the ANS assessment module 203 may be further configured to call the performance/strain correlation module 204 once the ANS assessment is complete.

The performance/strain correlation module 204 is program code stored in memory and executable by a processor to receive the cognitive exercise results from the cognitive testing module 202, or retrieve the cognitive exercise results from memory, and correlates the results with physiological measurements (including, in some examples. changes thereof). For instance, where the physiological measurements are indicative of cognitive exertion, signifying a point where the brain is having difficulty carrying out certain exercises, the performance/strain correlation module 204 may then compare the cognitive exercise results at that given time to see if the patient's performance level to the cognitive exercise is decreasing. The performance/strain correlation module 204 may assess exercise performance as a function of time, and physiological measurements as a function of time, and determine a first time where the patient has both physiological measurements indicative of cognitive exertion, and a change in cognitive exercise performance level indicative of, for instance, fatigue or cognitive difficulties.

The performance/strain correlation module 204 may then call the cognitive function evaluation module 205.

The cognitive function evaluation module 205 is program code stored in memory and executable by a processor to evaluate the cognitive function of a person as a function of the correlation results received from the performance/strain correlation module 204, or that is retrieved from memory (stored earlier by the performance/strain correlation module 204). In some examples, the cognitive function evaluation module 205 may evaluate the cognitive function from the physiological measurements and the cognitive exertion gauged from the physiological measurements. This may be the case when the apparatus 100 does not measure performance level of a subject to a cognitive exercise, or when, in one instance, the subject does not perform a cognitive exercise (such as when the subject is conducting routine activities and the apparatus is monitoring the patient for cognitive exertion so that the patient does not overtax his or her brain).

The cognitive function evaluation module 205 compares the correlation of the performance/strain correlation module with a known constant, such as a performance index, or a previous correlation from the same patient or a group of patients having the same cognitive disorder (with, e.g., a same or similar recovery time) to evaluate the patient's cognitive function. The evaluation of the cognitive function of the patient may include evaluating an improvement or deterioration of the patient's condition.

For instance, when the cognitive function evaluation module 205 receives a time stamp from the performance/strain correlation module 204 indicative of the first time the patient had shown signs of drop in responsiveness when performing the exercise and a change in physiological measurements indicative of cognitive exertion, then the cognitive function evaluation module 205 may compare this time with that of the patient when he or she last performed the test to see if there is an improvement/deterioration of the patient's cognitive function as a function of the measured time. The cognitive function evaluation module 205 may output a result indicative of the improvement/deterioration, and of the degree of the improvement/deterioration.

Similarly, when the apparatus 100 is used to evaluate the strain of a patient that is attempting to return to his or her routine activities, the architecture 201 may be further adapted to receive as input the time when the person gets to work, or starts a task at work. The cognitive function evaluation module 205 then receives a time stamp of the first time the patient had shown signs of a change in physiological measurements indicative of cognitive exertion. In some examples, this time stamp may be indicative of the total time the patient was at work or carrying out a given task. The cognitive function evaluation module 205 may then output a time reading to the user of when he or she first started to show signs of cognitive exertion. The cognitive function evaluation module 205 may calculate a daily average amount of time that the patient conducted a cognitive task before starting to show signs of cognitive exertion, the average calculated, over a period such as a week. The cognitive function evaluation module 205 may also output a suggested time to the user, the suggested time indicative of how much time the patient should on future days spend performing the measured cognitive task without risking pushing back the patient's recovery. It will be appreciated that the information output by the cognitive function evaluation module 205 may vary depending on the function of the apparatus 100 (e.g. used in a clinical setting, or as mobile apparatus to allow a patient to return to the patient's routine activities, etc.).

Figure 3:
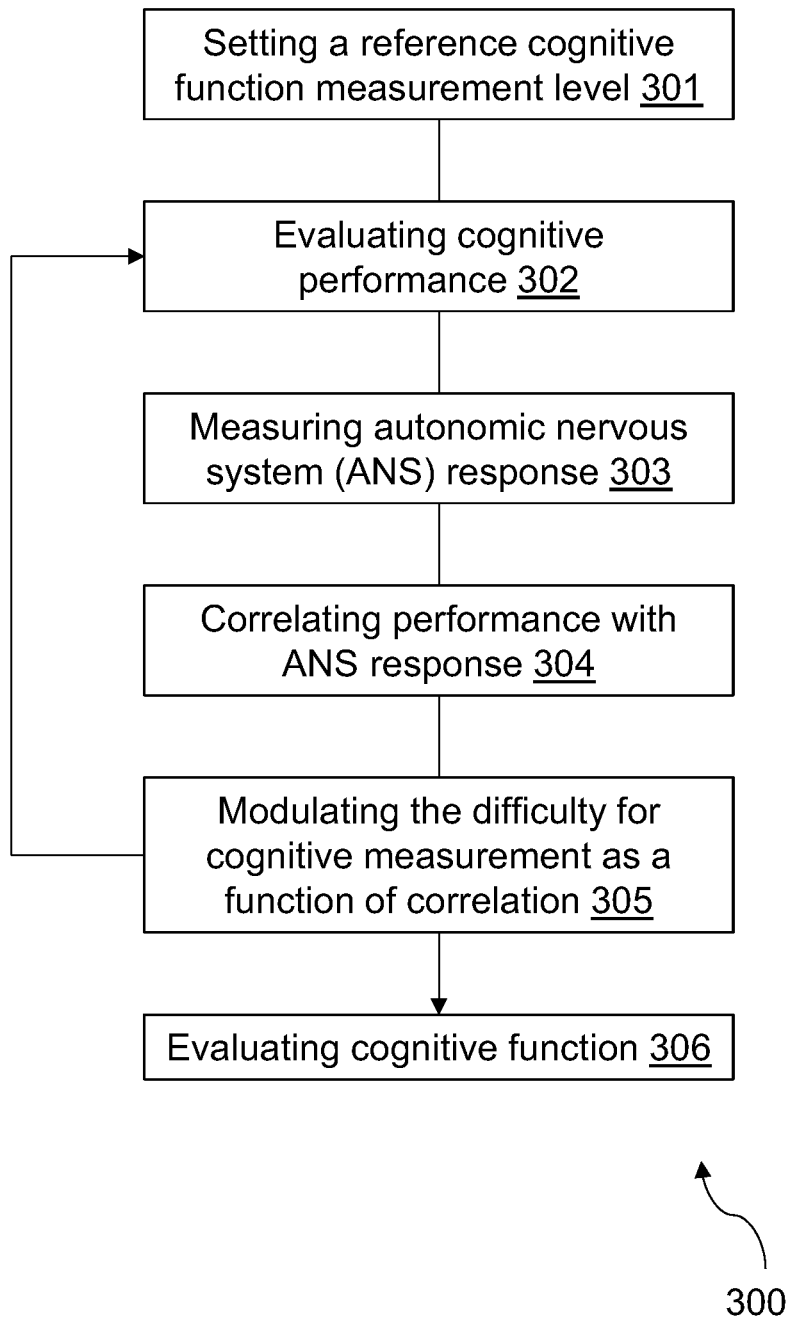
FIG. 3 is a flowchart diagram of an exemplary method for evaluating the cognitive function of a person while receiving feedback on changes relating to the autonomic nervous system of the evaluated person.

A Method of Evaluating Cognitive Function of a User:

Reference is now made to FIG. 3, illustrating an exemplary method 300 of evaluating the cognitive function of a person that measures a bodily function of that person, that bodily function controlled by the ANS.

In some embodiments, a level of the cognitive exercise is further set at step 301. The level may be, for instance, a difficulty setting, a type or exercise, or an exercise parameter to measure a specific function that is affected by the cognitive condition of the patient. The sort of cognitive exercise may also be selected at step 301.

The cognitive performance level of the patient is then evaluated at step 302. The performance level of the patient may be assessed as a function of the patient's ability to carry out the cognitive exercise. The cognitive exercise may be started and then the patient can start carrying out the exercise. The cognitive testing module 202 starts running, and the cognitive exercise commences. The readings/results of the cognitive exercise are obtained as a function of user input received by the cognitive exercise evaluator 105 (e.g. a user's response to the test, such as by pushing a button at a proper time). The patient's responsiveness to the cognitive exercise provides a first indicator of the cognitive health of the patient.

Certain of the patient's bodily functions that are controlled by the ANS are measured at step 303. The physiological measurements may be taken at the same time as the cognitive performance level is evaluated (physiological measurements may also be taken before and/or after the cognitive exercise). Therefore, both step 302 and step 303 may be carried out at the same time. The physiological measurements may be taken by the physiological measurement device 104. The physiological measurements may be processed by the ANS assessment module 203 to determine if there is a change in physiological measurements that provides an indication of cognitive exertion. For instance, as the patient grows mentally tired when performing the cognitive exercise, his heart rate may increase. This increase in heart rate may provide an indication of when the patient is starting to strain his or her mind when performing the cognitive exercise. The time stamp indicative of the first signs of cognitive exertion (and of different levels of cognitive exertion, such as light, mild and heavy) may be stored in memory for future analysis by, for instance, the performance/strain correlation module 204. In some examples, this time stamp may also be transmitted to the intelligence module, as described herein, wherein this time stamp may be used to generate adaptive cognitive exercise as a function of this observed data.

The physiological measurements provide a further indication of the cognitive health of the patient, where this second data set is then further correlated with the cognitive exercise performance level of the patient in order to yield a more complete portrait of the patient's cognitive health and performance. Therefore, cognitive performance to the cognitive exercise is then correlated with the physiological measurements at step 304. The correlation is performed by the performance/strain correlation module 204, called by the ANS assessment module 203 and/or cognitive testing module 202.

It will be understood that other measurements of the patient may also be taken at step 303. For instance, by performing biomechanical muscular monitoring of the patient, and comparing the biomechanical muscular data of the patient while performing the cognitive exercise with expected biomechanical muscular results, this may further provide an indication as the patient's cognitive health. Similarly, biomechanical muscular responsiveness may also further the diagnosis as to the patient's cognitive health. In other examples, by monitoring brain activity of the patient (e.g. monitoring level of brain oxygenation, by brain oximetry, fMRI, VEP, electrocerebellogram, etc.), and comparing the brain activity data of the patient while performing the cognitive exercise with expected brain activity results, this may further provide an indication as the patient's cognitive health. Similarly, biomechanical muscular responsiveness may also further the diagnosis as to the patient's cognitive health.

In response to the patient's responsiveness or performance level when carrying out the cognitive exercise, and/or while considering the cognitive exertion or stress of the patient as indicated by the physiological measurements, the difficulty of the cognitive exercise performed may be modulated at step 305. For instance, if the patient does not experience any cognitive exertion and is outperforming the cognitive exercise, the difficulty of the exercise may be increased. However, in one example, if the patient is instead experiencing cognitive exertion, as indicated by the physiological measurements, and/or the patient is not properly carrying out the cognitive exercise, then the difficulty level of the cognitive exercise may be lowered. Once the difficulty of the cognitive exercise has been modulated, then the patient's cognitive performance may be further evaluated at this modulated level at step 302, carrying out steps 302 to 305 at the new level of difficulty.

Once sufficient data on the patient has been gathered by performing the cognitive exercise and by monitoring the patient's physiological measurements before, during and after performance of the cognitive exercise, the cognitive function of the patient may be evaluated at step 306. The cognitive performance level may be assessed by the cognitive function evaluation module 205, called by the performance/strain correlation module 204 once the correlation is complete at one or different difficulty levels of cognitive exercise.

Figure 4:
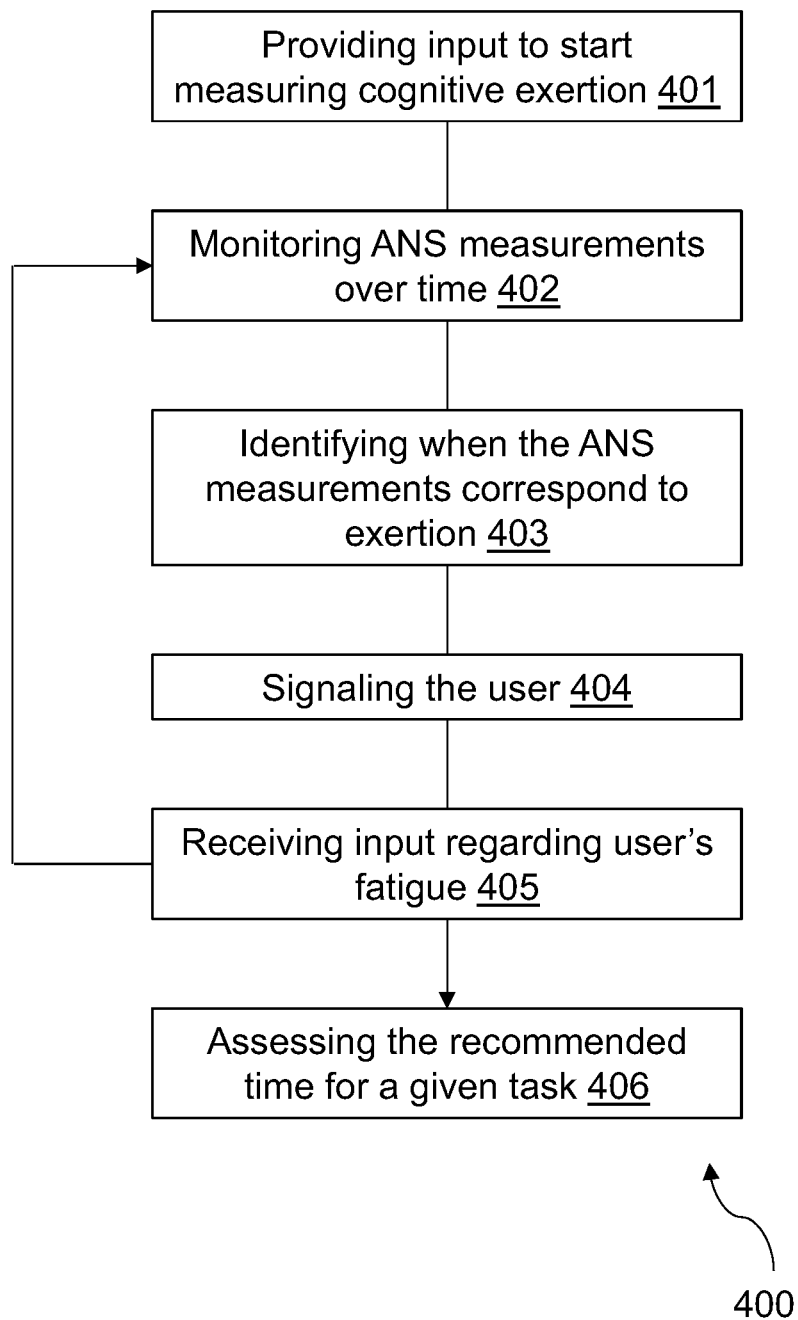
FIG. 4 is a flowchart diagram of an exemplary method for assessing the recommended time that a user suffering from cognitive impairment should spend carrying out a cognitive task.

A Method of Avoiding Deleterious Cognitive Exertion or Exertion that can Impact Recovery of Cognitive Function:

FIG. 4 illustrates an exemplary method 400 of assessing and/or measuring the exertion of a user in order to avoid the user overexerting him or herself mentally. This method may be performed, for instance, when a patient who has suffered from cognitive impairment (e.g. a concussion, a stroke, an aneurism, etc.) and is strengthening, without necessarily the presence of a medical practitioner, his or her cognitive function. In other examples, the patient may be trying to get back into a regular routine following an injury that affects the patient's cognitive function. However, the patient does not want to overstrain him or herself, and risk relapsing or prolonging recovery due to undesirable overexertion of the brain. In some examples, physical exertion may impact upon the recovery of cognitive function of the patient.

Similarly, in some examples, by monitoring bodily functions of the patient tied to physical exertion (e.g. stress; exercise), and by comparing these observed physiological measurements with a given permissible range for that given bodily function so as not to exert him or herself to an extent that the exertion will impact recovering from cognitive impairment, it is possible to assess if the patient is exerting him or herself to an extent that the exertion will impact recovery from cognitive impairment. If the observed physiological measurements are beyond the permissible range, then the patient may be alerted (e.g. a text message received on a smartphone; an email; a pushed notification; etc.) to cease the activity (e.g. physical, cognitive) so as not to impair recovery of cognitive function.

The method assesses the cognitive exertion of the patient during a cognitive task and informs and/or warns the patient when signs of overexertion are present by monitoring the patient's physiological measurements as explained herein.

The user (e.g. the patient) may first indicate when the cognitive task begins at step 401. For instance, the user may indicate when the user enters the office space, or starts a demanding cognitive task (e.g. writing program code, performing mathematical operations, writing a thesis paper, etc.). When the user is training his cognitive ability, the user may indicate when the cognitive training exercise begins. This input is processed by the apparatus 100 to begin monitoring one or more bodily functions regulated by the ANS. The input indicating the start of the activity may therefore call the ANS assessment module 203 that begins assessing the physiological measurements of the user.

The physiological measurements of the user are then assessed over time at step 402, while the user is performing the cognitive task(s).

The ANS assessment module 203 may established (or may have established) a baseline (e.g. resting heart rate) for the monitored physiological measurement, and establishes the changes from that baseline or threshold. For instance, the baseline or threshold may be established at the beginning of, or prior to starting, the cognitive exercise. The ANS assessment module 203 then assesses the physiological measurement data for indication of cognitive exertion at step 403, such as when the difference between the current readings and the baseline as computed by the ANS assessment module 203 is great enough to indicate possible cognitive exertion (e.g. heart rate over a certain level for a person of a given age).

The apparatus 100 may then signal the user of possible cognitive exertion at step 404. In some examples, the signal is a warning, heeding that the user stop immediately the cognitive task the user is carrying out. In other examples, the signal instead may request feedback from the user. For instance, when the ANS assessment module 203 begins to detect signs of cognitive exertion, the ANS assessment module 203 may request that the user provide feedback on his or her fatigue at step 405. The apparatus 100 may address, via display 106, a question to the user, e.g. "Are you feeling tired?" The user may respond by <YES> or <NO>. If the user selects <YES>, then the apparatus 100 may urge the user to immediately cease carrying out the cognitive task he or she is currently undertaking. If the user selects <NO>, then the apparatus 100 may simply output a warning to slow down or take a break. In some examples, the question may be phrased to ask the user when does the user, performing physical activity, start feeling signs of cognitive fatigue, or cognitive exertion. The apparatus may then record when the user provides input indicative of signs of cognitive exertion, and can record at what level of physical exertion (e.g. by recording the heart rate, or heart rate maintained at a level for a given time) that the signs of cognitive exertion present themselves. The apparatus 100 may then continue to monitor the physiological measurements of the user at step 402 for signs that the physiological measurements for that bodily function return to, or are close to, that of the user at rest. Steps 402 to 405 may then be repeated until user stops carrying out the cognitive task, either because the task is complete, or the user surpasses a recommended cognitive exertion level as assessed the ANS assessment module 203.

In some examples, the user input may not be the user answering questions, but a mechanism for monitoring the user's ability to perform the given cognitive function. For instance, when the user's cognitive task involves typing on a keyboard, the mechanism may monitor the number of keystrokes as a function of time, and assess when the rate of keystrokes drops. This may provide feedback on the user's performance level of the cognitive task at work. In these examples, the cognitive testing module 202 may receive the keystroke information and assess cognitive performance of the user as explained herein. Moreover, the performance/strain correlation module 204 may correlate the user's cognitive performance level with the physiological measurements as explained herein.

The cognitive function evaluation module 205 may then be called to evaluate the recommended time that the user should pass doing that specific cognitive task at step 406 as a function of the physiological measurements. For instance, the cognitive function evaluation module 205 may assess, based on the physiological measurement data collected by the ANS assessment module 203, that after three hours of working on the computer (based on one day of work, or an average of several work days), the user has difficulty performing the task (e.g. based on received user input) and/or the user's cognitive exertion goes over the recommended level. For example, to not impact recovery, cognitive function evaluation module 205 may then output for the user a recommended time that the user should be performing the cognitive task. Moreover, the cognitive function evaluation module 205 may retrieve previous cognitive function evaluation(s) of the user stored in memory and output information, after comparing the retrieved values of the previous cognitive function evaluations with the current values, regarding if the user's cognitive function is improving or regressing.

In some embodiments, the physiological measurement data may also be transmitted and monitored remotely by a physician or other medical professional. In this example, the medical professional may view the data and identify when the physiological measurement data is indicative of cognitive exertion that could be deleterious to the patient. The physician may then contact the patient (e.g. via text-message; email; alert appearing on the mobile device; etc.) to, for example, inquire on the patient's activity. The medical professional may then recommend that the patient cease whatever activity the patient is undertaking in order to avoid overtaxing his or her cognitive ability that may hinder, for example, recovery from an injury. In some examples, the recommendation may also be generated and transmitted to the patient by the apparatus itself, based, for instance, on the information provided in the created and stored profile of the patient.

Eye Tracking:

The cognitive apparatus may also have an eye-tracking function, the cognitive exercise involving the use of an image or a plurality of images.

Figure 10:
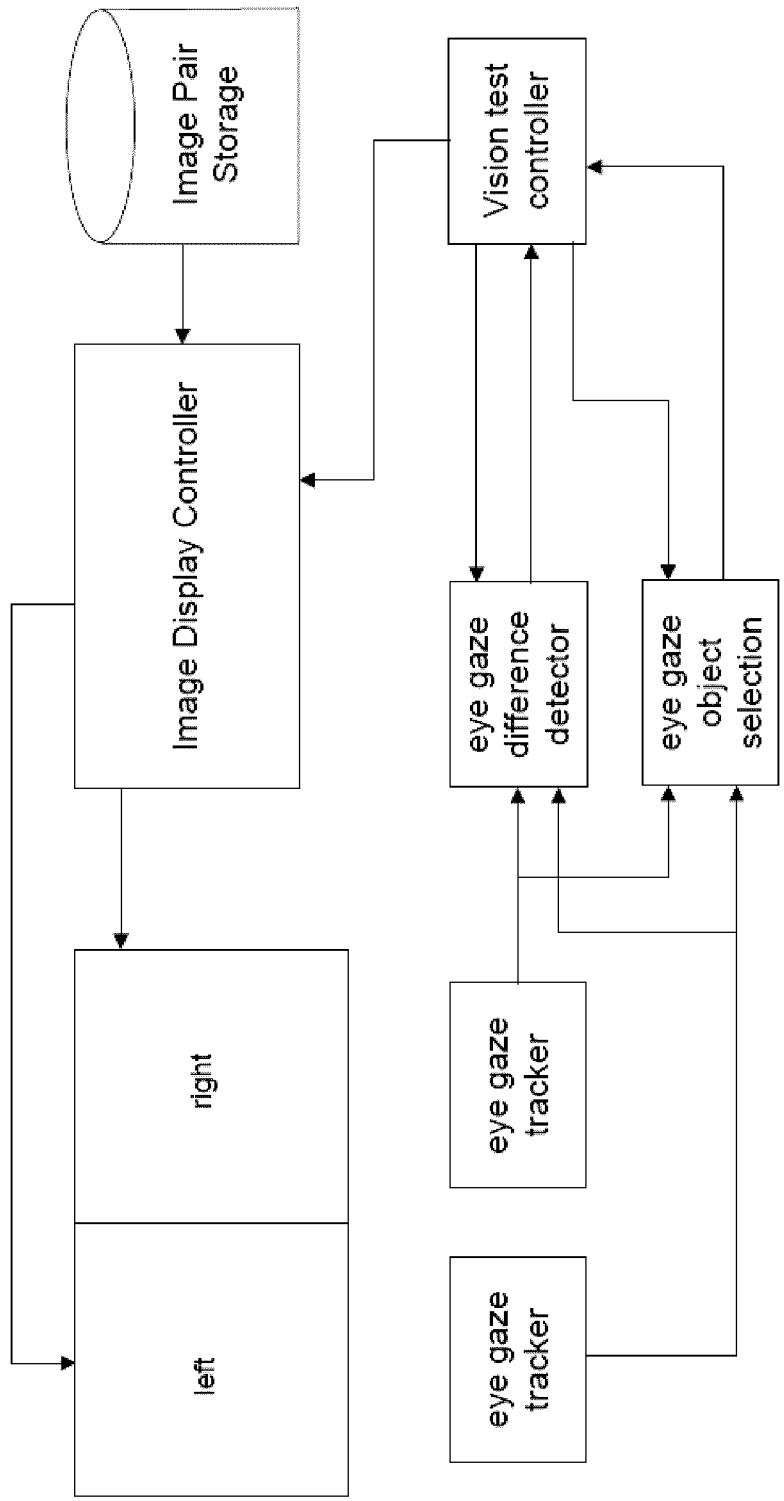
FIG. 10 is a block diagram of an exemplary vision testing apparatus for vision monitoring used with a cognitive testing apparatus.

As shown in FIG. 10, a display device may be configured to display left and right eye images separately to each eye. This display device can be a head-mounted display, a display that is fixed in position with respect to the subject (for example with the subject's head being positioned in or on a guide) or without any positioning mechanism (using the subject's cooperation to be positioned within suitable viewing range). The display can use two different screens for each eye (or different sides of a common screen), or, as is known in the art of stereoscopic displays, autostereoscopic screens, color lens glasses, polarizer glasses (for polarized light displays) or LC shutter glasses (for page-flip displays) can be used. In some examples, visual display can also be done through augmented reality, holograms and/or mixed reality.

Eye gaze trackers for each eye are provided in association with the display for detecting the gaze direction of each eye. Such eye gaze trackers are known in the art per se, and need not be described in further detail herein.

The image display controller retrieves images from a storage (or generates using software) suitable image pairs for conducting the vision test. The vision test controller signals the image display controller to generate image pair for a desired test. In some embodiments, the apparatus can be dedicated to a single type of vision test.

When the vision test controller selects a vision test, in the embodiment of FIG. 10, a signal is provided to the eye gaze difference detector and the eye gaze object selection modules. The signal provided to these modules defines the detection criteria, and the output of these modules is the detection result according to the criteria provided. It will be appreciated that a different arrangement of eye gaze tracker signal processing can be arranged.

The eye gaze difference detector detects a difference in the gaze direction between the two eyes. In the mentioned tests, such as the cover test, punctum proximum test and the prism test, the change in images results in a sudden change in where the gaze direction such that there is a sudden difference between the gaze direction between the eyes. The kind of change to be detected can be provided in the signal to the detector provided by the vision test controller.

The eye gaze object selection module is used for vision test in which the subject is expected to fuse objects within the left eye and right eye images. In these kinds of tests, the images comprise typically a number of objects. The subject may be requested to look at a specific object, such as the object appearing behind a middle object, or an object in the middle. Eye tracking can discern whether the subject is looking at the object requested by the test or not, and thus signal an object selection result to the vision test controller.

It will be appreciated that the eye gaze object selection can also include subject input to select an object instead of using eye gaze tracker input.

Figure 6A:
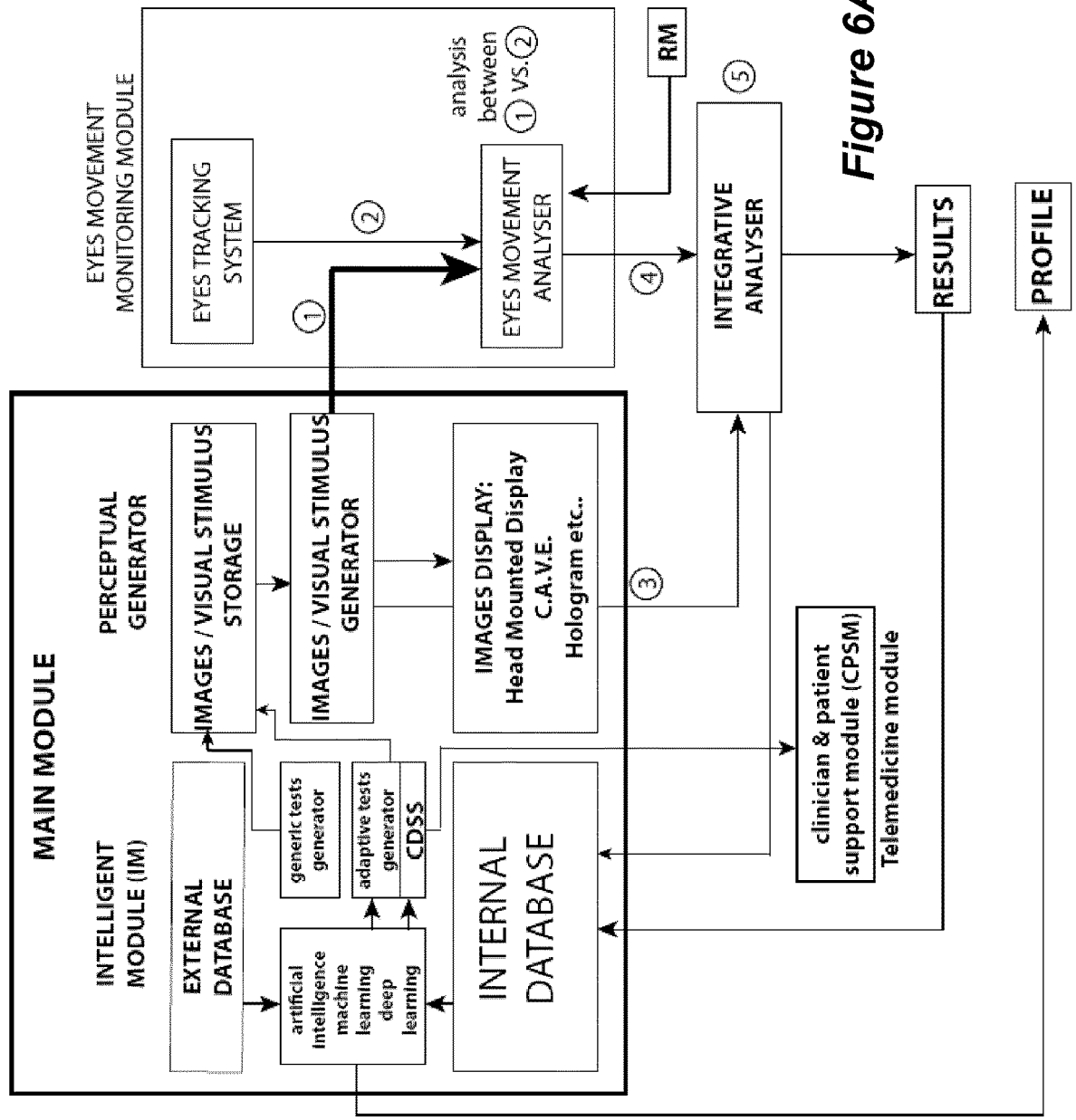
FIG. 6A is a block diagram of an exemplary apparatus for evaluating cognitive function with an image display.

Reference is now made to FIG. 6A, illustrating an exemplary apparatus for evaluating cognitive function of a patient by measuring responsiveness of a patient and by comparing the observed responsiveness with expected responsiveness.

By responsiveness data, it is meant, for example, data corresponding to the eye movement of the patient, data corresponding to the physiological monitoring of the patient (e.g. monitoring the patient's bodily functions controlled by the patient's autonomic nervous system), data corresponding to the patient's biomechanics/muscular responsiveness, or data corresponding to the patient's brain activity. Different response evaluators may be used to measure the patient's given responsiveness to a given exercise. For the purposes of the examples shown in FIGS. 6A to 6D, the response evaluator has an eye tracking system and eye movement analyzer to track and analyse the eye tracking of the patient. However, it will be understood that the apparatus may have any response evaluator for measuring and analyzing a given or different response of the patient (depending upon what response is being observed), or a response evaluator that is configured with instruments to measure multiple types of responses (e.g. eye movement, physiological monitoring, biomechanics, brain activity, etc.) from the patient as described herein.

The apparatus is capable of improving the accuracy of the generated cognitive exercise by adapting the cognitive exercise by comparing the observed responsiveness data with expected responsiveness data for the given cognitive exercise. This comparison provides the apparatus with additional information as to the patient's capacity to perform the cognitive exercise, reflective upon the patient's cognitive health.

The program code architecture for testing cognitive function may have a main module that extracts, from an internal database (or in some examples, and/or an external database), cognitive exercises (e.g. image pairs for conducting cognitive tests). The main module may process the data through program code including, for instance, a machine learning algorithm or deep learning algorithm, and the result of the processing may yield an adaptive cognitive exercise (e.g. image pairs for conducting cognitive tests) executed by the perceptual generator to produce the images on the display. The information may also be sent to the clinical decision support system, so that the information may be shared with the clinician and patient support module. The cognitive tests can be generated by the generic tests generator. The tests may also be generated by the adaptive tests generator, where the adaptive test generator may communicate with a clinical decision support system (CDSS), where the tests are adapted as a function, for instance, of input received externally from a clinician and patient support module (CPSM) or telemedicine module, where, for example, a medical professional or medical practitioner may provide input (in some examples remotely) to tailor or to generate specific cognitive tests. The adaptive test generator may also communicate with an intelligence module that can send instructions to adapt the test as a function of previous results. In some examples, the cognitive testing apparatus may be used at, for example, the home of the patient, where the supervising medical practitioner may provide input remotely (e.g. at his or her office), such as suggesting certain cognitive exercises to be carried out by the patient, where the medical practitioner can then supervise the carrying out of the tests remotely.

The test generator (generic and/or adaptive) may then retrieve test information from image/visual stimulus storage, storing in memory image data for generating different images associated to different cognitive tests. The image/visual stimulus generator then carries out the instructions associated or sent by the test generator (generic and/or adaptive), retrieves the appropriate image data corresponding to the test (e.g. such as by analyzing metadata associated with the image data) and processes the image data as well as, e.g., instructions to tailor the image data as a function of the test parameters, for generating the images on a stimulus output interface, such as the image display (e.g. head mounted display; C.A.V.E., hologram, etc.). As described herein, the stimulus output interface is an interface to provide stimulus corresponding to the given cognitive exercise. The stimulus produced on or by the stimulus output interface may be, but is not limited to, visual stimulus, auditory stimulus, haptic stimulus, etc.

The apparatus for evaluating cognitive function may also have an eye movement monitoring module. The eye movement monitoring module has a vision tracker (vision tracking system) and an eye movement analyzer. The vision tracker identifies and tracks the eye movement of the patient that is conducting the cognitive exercise. The eye tracking data is then sent to the eye movement analyzer.

Image/visual stimulus storage may also contain data, along with the image data, relating to the expected eye movement that would be observed in, e.g., a healthy patient when carrying out the exercise. The image/visual stimulus generator may also extract from storage the expected eye movement data. The extracted expected eye movement data is then transmitted by the image/visual stimulus generator to the eye movement analyzer.

The eye movement analyzer receives and compares the expected eye movement data and the eye tracking data. The analysis of the eye movement analyzer yields comparison data that provides information regarding the patient's eye movement versus the expected eye movement for a given cognitive exercise. This provides an additional indication if the patient is responding to visual stimulus that is being presented to the patient on the image display.

In some embodiments, the apparatus may have a response module, connected to the eye movement analyzer, that receives input from a user input interface, for receiving input from the user when conducting the cognitive exercise (e.g. the response module transmits a signal to the eye movement analyzer when the user selects a button or provides input; the eye movement analyzer, upon receipt of the input, can then start comparing expected versus observed eye movement data following receipt of the signal).

The comparison data is then sent by the eye movement analyzer to the integrative analyzer. The integrative analyzer also receives image parameter data (e.g. size, geometry, psychophysics, color, angle, spatial shift) from the image/visual stimulus generator. The image parameter data may correspond to the nature of the cognitive test being performed. The integrative analyzer analyses the comparison data as a function of the image parameter data to provide result data as a function of the image parameters, and the expected eye movement.

The result data (i.e. results) is then transmitted by the integrative analyzer to the intelligence module of the main module, that, as a function of other data received on the patient (e.g. performance when conducting the cognitive test; physiological parameters; brain function) may be processed by the intelligence module to generate a cognitive evaluation of the patient (e.g. profile of the patient). The intelligence module may also communicate with the CDSS module, or the CDSS module that is in communication with the adaptive test generator, to transmit the profile information or the result information to the CDSS module. The CDSS module may then transmit this information to the CPSM module, where the remote medical practitioner may have access to the information.

Figure 6B:
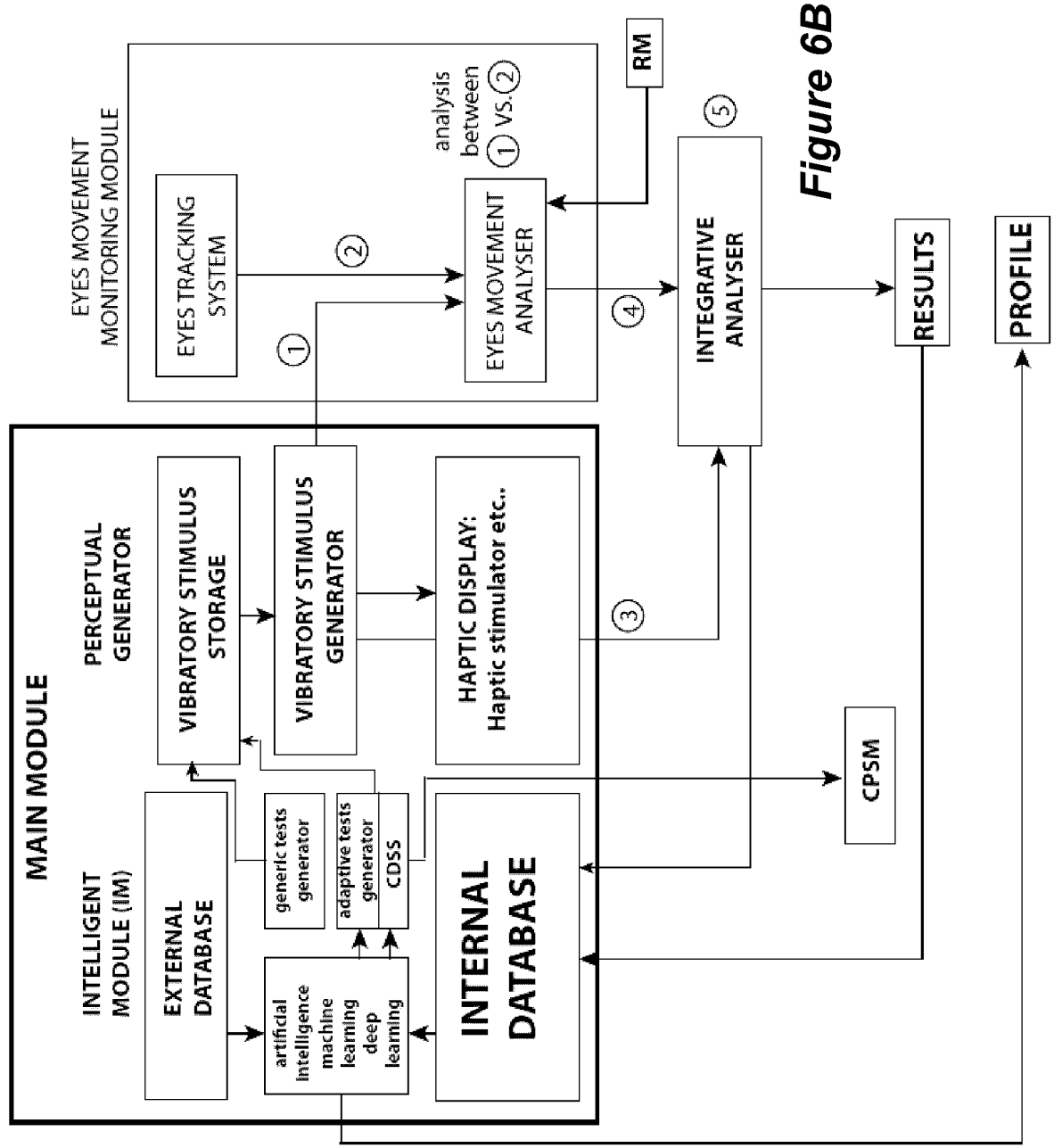
FIG. 6B is a block diagram of an exemplary apparatus for evaluating cognitive function with a haptic stimulator.

In some embodiments, as shown in FIG. 6B, the main module may instead have stored in memory, data to generate a haptic response (e.g. touch) from a patient using, for example, a haptic stimulator. The haptic stimulator may be integrated to a visual display. In this example, the vibratory stimulus generator retrieves from storage the vibratory stimulus data as a function of information or instructions received by the test generator (e.g. generic or adaptive).

In the example of FIG. 6B, the haptic stimulation may trigger eye movement. Therefore, the eye movement may be tracked, analyzed and compared, while taking into account the haptic stimuli generated, to provide tailored eye movement data.

Figure 6C:
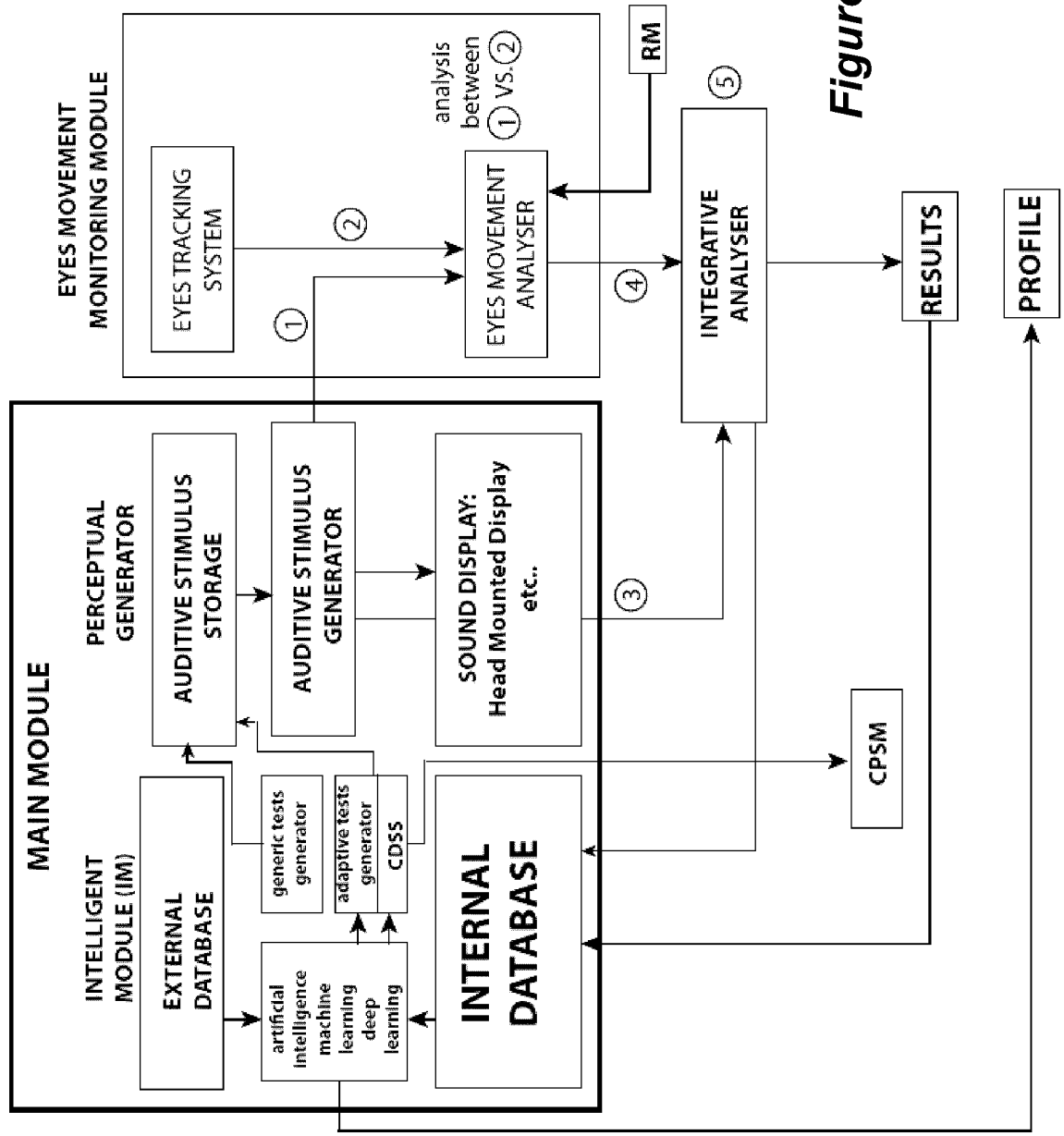
FIG. 6C is a block diagram of an exemplary apparatus for evaluating cognitive function with a sound generator.

Similarly, as shown in FIG. 6C, in some embodiments, the perceptual generator may instead produce, with the sound display (e.g. head mounted display with speakers) sounds that trigger eye movement from the patient. The sound data is retrieved from storage by the auditory stimulus generator as a function of the information and/or instructions received from the test generator (e.g. generic or adaptive), and processed by the auditory stimulus generator to have the sound display generate the sounds. The eyes of the patient may therefore move as a function of the sound. Therefore, the result data is generated as a function of the sound produced.

Figure 6D:
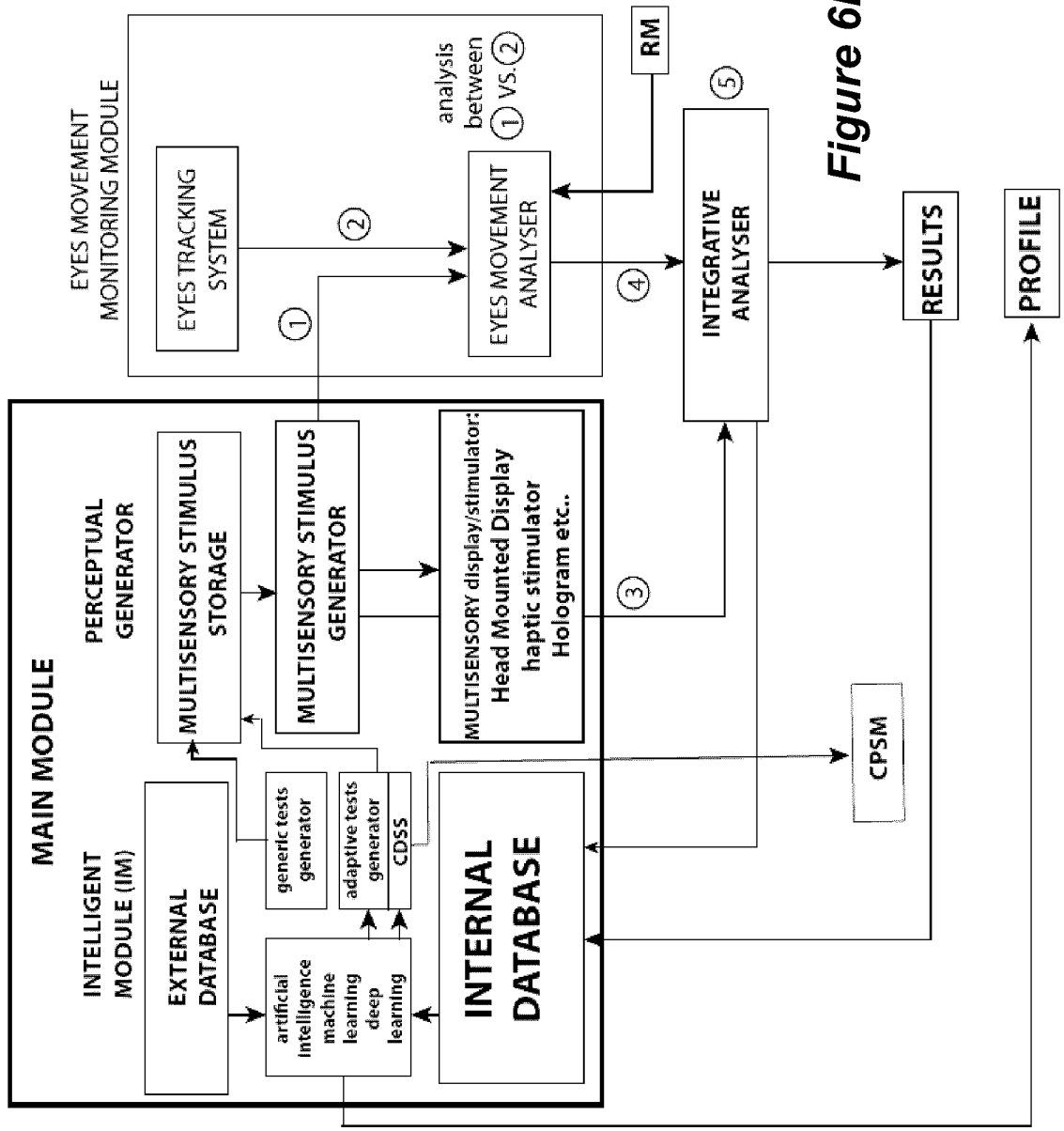
FIG. 6D is a block diagram of an exemplary apparatus for evaluating cognitive function with a multisensory stimulator.

In some examples, such as in FIG. 6D, the perceptual generator may produce multiple forms of stimuli. The storage may store data to produce multiple forms of stimuli, the data retrievable by the multisensory stimulus generator to have the multisensory display/stimulator produce the stimuli as a function of the multisensory data and the cognitive test that is generated.

EXAMPLES OF VISUAL COGNITIVE EXERCISES USED WITH VISION TRACKING

Example 1: Cover Test

In the example of a cover test performed using a display (e.g. a head mounted display), images are presented to each eye, as is performed for virtual reality. Then, one image presented to one eye will disappear (or be dimmed), the process repeated for the other eye, where the system alternates between both eyes. As the disappearing or dimming alternates between the images for each eye, the eye movement monitoring module tracks and analyses eye movement with respect to the expected eye movement data, and sends the comparison data to the integrative analyzer. In turn, the integrative analyzer transmits the result data to the intelligence module.

The intelligence module may then provide instructions for the adaptive test generator to generate an adapted sequence of the test (e.g. alternating disappearance or dimming of the images with a spatial shift). The expected eye movement data for the adapted test is also transmitted to the eye movement analyzer. The image presented to one eye is offset by a few degrees of the field of view of the patient, during, e.g. each alternation, without the patient being aware of such (e.g. in some examples, only the image presented to one eye may be offset). The eye tracking system observes the eye movement, and produces eye tracking data. The eye movement analyzer compares and analyses the eye tracking data and the expected eye movement data. When the movement of the eyes tracked by the eye tracking system equals zero, the eye movement analyzer transmits the information regarding the spatial shift that resulted in the patient's eyes not having any eye movement, this information sent to the integrative analyzer, that in turn yields tailored correlation data (a result) that is transmitted to the intelligence module which can generate a profile.

Example 2: Motor Punctum Proximum Test

The motor punctum-proximum test can be performed using a display (e.g. a head-mounted display), where a static visual object/stimulus is presented stereoscopically. The object or stimulus is then virtually and progressively brought closer to the eyes. As the object/stimulus is brought closer, the images/visual stimulus generator retrieves from storage and transmits to the eye movement analyzer the expected oculomotor response that is compared to the oculomotor response measured by the eye tracking system. When the measured eye movement corresponds to the expected eye movement, the information regarding the object's distance that results in the correspondence between the expected and measured eye movement is sent to the integrative analyzer that generates result data (a result) and transmits this data to the intelligence module which can generate a profile.

Example 3: Fusional Punctum Proximum Test

This test occurs after a punctum proximum test. In the framework of a fusional punctum proximum test performed using a display (e.g. head mounted display), a static visual object/stimulus is presented stereoscopically. The object or stimulus is then virtually and progressively brought closer to the eyes. As the object/stimulus is progressively brought closer, the image/visual stimulus generator transmits information to the eye movement analyzer, this information representing the oculomotor response obtained during the motor punctum proximum test. When the user activates the response module, the information regarding object distance are sent to the integrative analyzer which compares this information with the oculomotor response obtained during the motor punctum proximum test, and generates the result data (a result), and sends this data pertaining to the result to the intelligence module which can generate a profile.

Example 4: Passive Prism Effect Test

The passive prism effect test may be performed using a display, e.g., a head-mounted display. A static visual object/stimulus is presented stereoscopically. Then, an alternative visual occlusion/presentation of the image is performed (the visual occlusion and presentation is done simultaneously for both eyes, and not alternatively). During the occlusion, a spatial shift occurs to the image presented to the right eye, the left eye, or the images presented to both eyes that are used to obtain the stereoscopic effect. During this process, the image/visual stimulus generator retrieves from storage and transmits to the eye movement analyzer information regarding the expected oculomotor response, that will be compared to the oculomotor response measured by the eye tracking system. The image/visual stimulus generator transmits information regarding the spatial shift to the integrative analyzer. When the measured eye movement corresponds to the expected eye movement, the eye movement analyzer sends the comparison data to the integrative analyzer that processes the comparison data with the spatial shift data to generate tailored correspondence data (a result), transmitting this data to the intelligence module which can generate a profile.

Example 5: The Active Prism Effect Test

The active prism effect test may be performed using a display, e.g., a head-mounted display. A static visual object/stimulus is presented stereoscopically. Then, an alternative visual occlusion/presentation of the image is performed (the visual occlusion and presentation is done simultaneously for both eyes, and not alternatively). During the occlusion, a spatial shift is made to the image presented to the right eye, the left eye, or the images presented to both eyes that are used to obtain the stereoscopic effect. During this process, the image/visual stimulus generator retrieves from storage and transmits to the eye movement analyzer information regarding the expected oculomotor response, that will be compared to the oculomotor response measured by the eye tracking system. When the response module (user input interface), connected to the eye movement analyzer is activated by the user, the information regarding eye movement relating to eye movement is transmitted from the eye tracking system to the eye movement analyzer, the eye movement analyzer comparing the measured eye movement to the expected eye movement. The comparison data is transmitted to the integrative analyzer that calculates and generates result data (a result), transmitting the result data to the intelligence module which can generate a profile.

Figure 7:
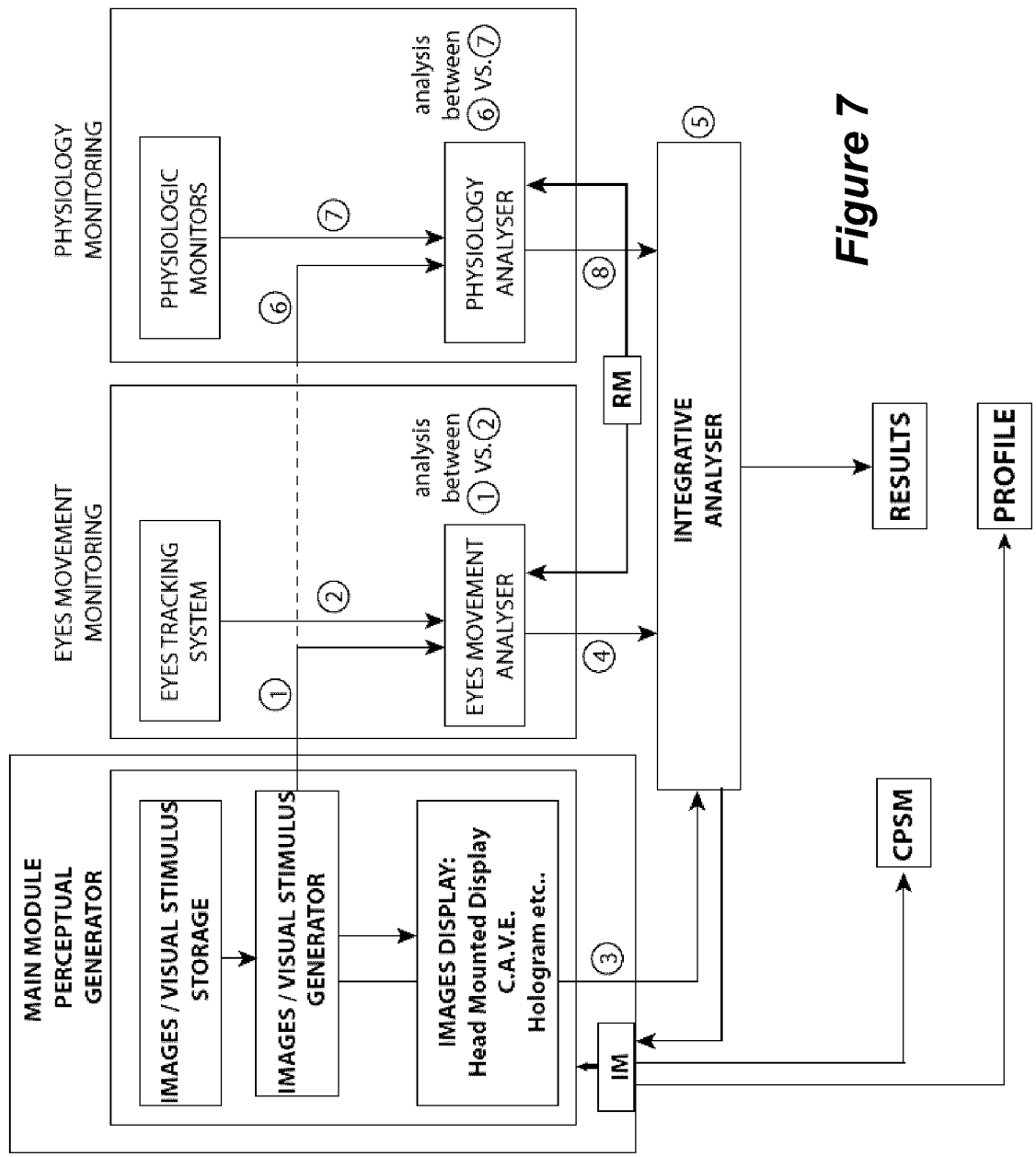
FIG. 7 is a block diagram of an exemplary apparatus for evaluating cognitive function with eye movement monitoring and physiology monitoring.

Combined Eye Tracking and Physiological Monitoring:

In some examples, as shown in FIG. 7, the apparatus for evaluating cognitive function may have a physiological monitoring function (i.e. measuring and analyzing physiological measurements), as described herein, combined with the eye tracking.

In these examples, storage may have, along with the stimuli data, expected physiological monitoring data corresponding to a given cognitive exercise (e.g. expected changes in heart rate as a function of the difficulty of the exercise). The image/visual stimulus generator may retrieve from memory the expected physiological data corresponding to the stimuli data retrieved for the given cognitive exercise.

Similarly, the physiologic monitor (i.e. the physiological measurement device 104) takes readings and generates physiological measurement data as the patient performs the given exercise. The physiological measurement data of the patient is transmitted to the physiological analyzer that receives the expected physiological data from the image/visual stimulus generator.

The integrative analyzer receives the comparison data of the physiological measurements, the comparison data of the eye movement, and the stimuli parameter data. The tailored comparative data produced by the integrative analyzer is transmitted to the intelligence module. The intelligence module is capable of providing a more accurate cognitive evaluation of the profile of the patient, as the cognitive performance data is analyzed in addition to the eye movement data and physiological measurement data.

Figure 8:
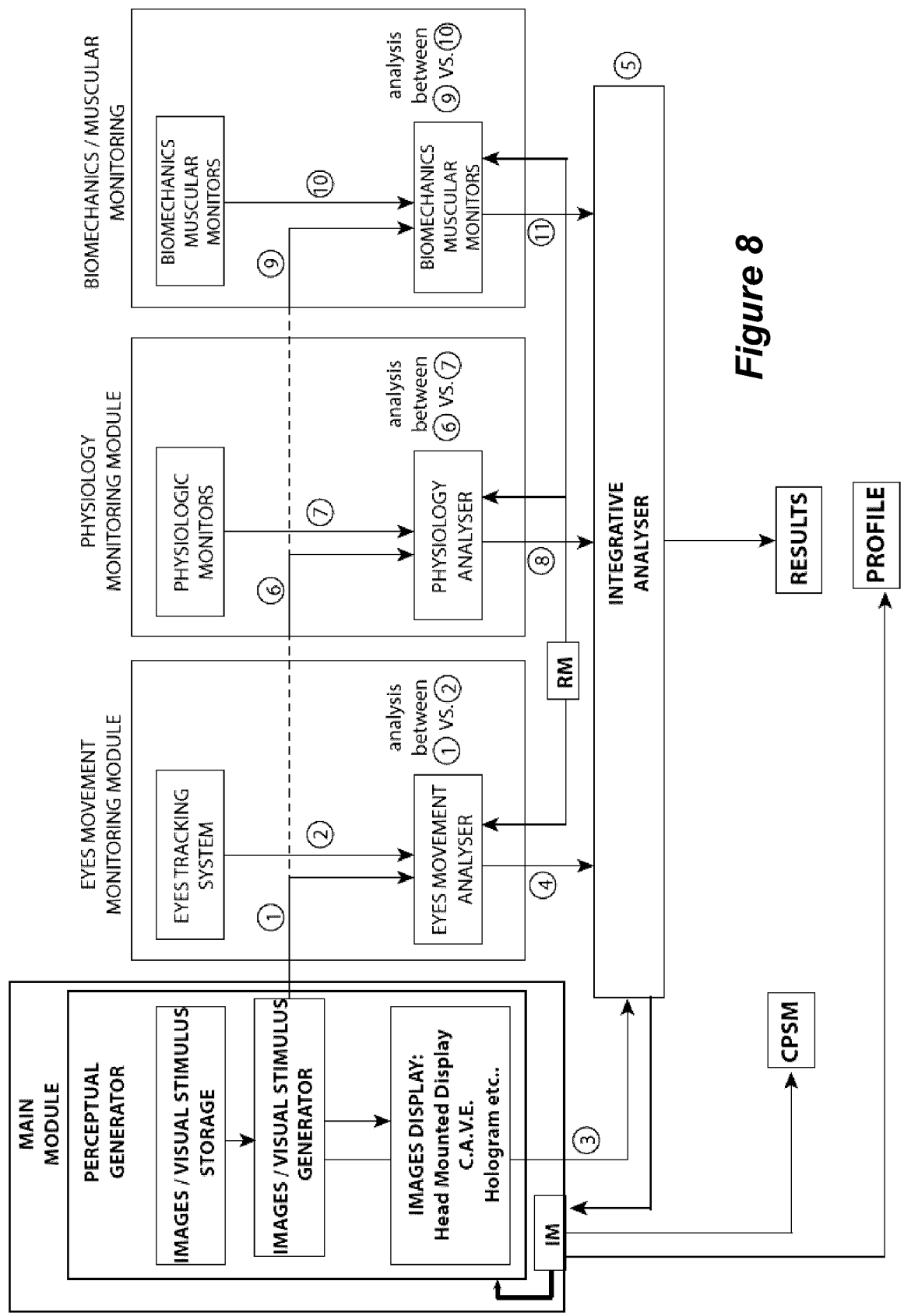
FIG. 8 is a block diagram of an exemplary apparatus for evaluating cognitive function with eye movement monitoring, physiology monitoring and biomechanics/muscular monitoring.

Combined Eye Tracking, Physiological Monitoring and Biomechanics/Muscular Monitoring:

In some examples, as shown in FIG. 8, the apparatus for evaluating cognitive function may have a biomechanics/muscular monitoring function, combined with the physiological monitoring function and/or the eye tracking. The apparatus may have a biomechanical muscular monitor and a physiology analyzer.

In these examples, storage may also have data related to biomechanics/muscular data for different cognitive exercises, along with the stimuli data. The image/visual stimulus generator may retrieve from memory the expected biomechanics/muscular data corresponding to the stimuli data retrieved for the given cognitive exercise.

The biomechanical muscular monitor may be an electromyogram, accelerometer, gyroscope, motion capture sensor, etc. obtaining biomechanical muscular data of the patient that is carrying out the cognitive exercise. The biomechanical muscular data of the patient is transmitted to the biomechanical analyzer that also receives the expected biomechanical muscular data from the image/visual stimulus generator.

The integrative analyzer receives the comparison data of the biomechanical muscular data, the comparison data of the physiological measurements, the comparison data of the eye movement, and/or the stimuli parameter data. The result data produced by the integrative analyzer is transmitted to the intelligence module. The intelligence module is capable of providing a more accurate cognitive evaluation of the profile of the patient, as the cognitive performance data is analyzed in addition to the biomechanical muscular data, the eye movement data and/or physiological measurement data.

Figure 5:
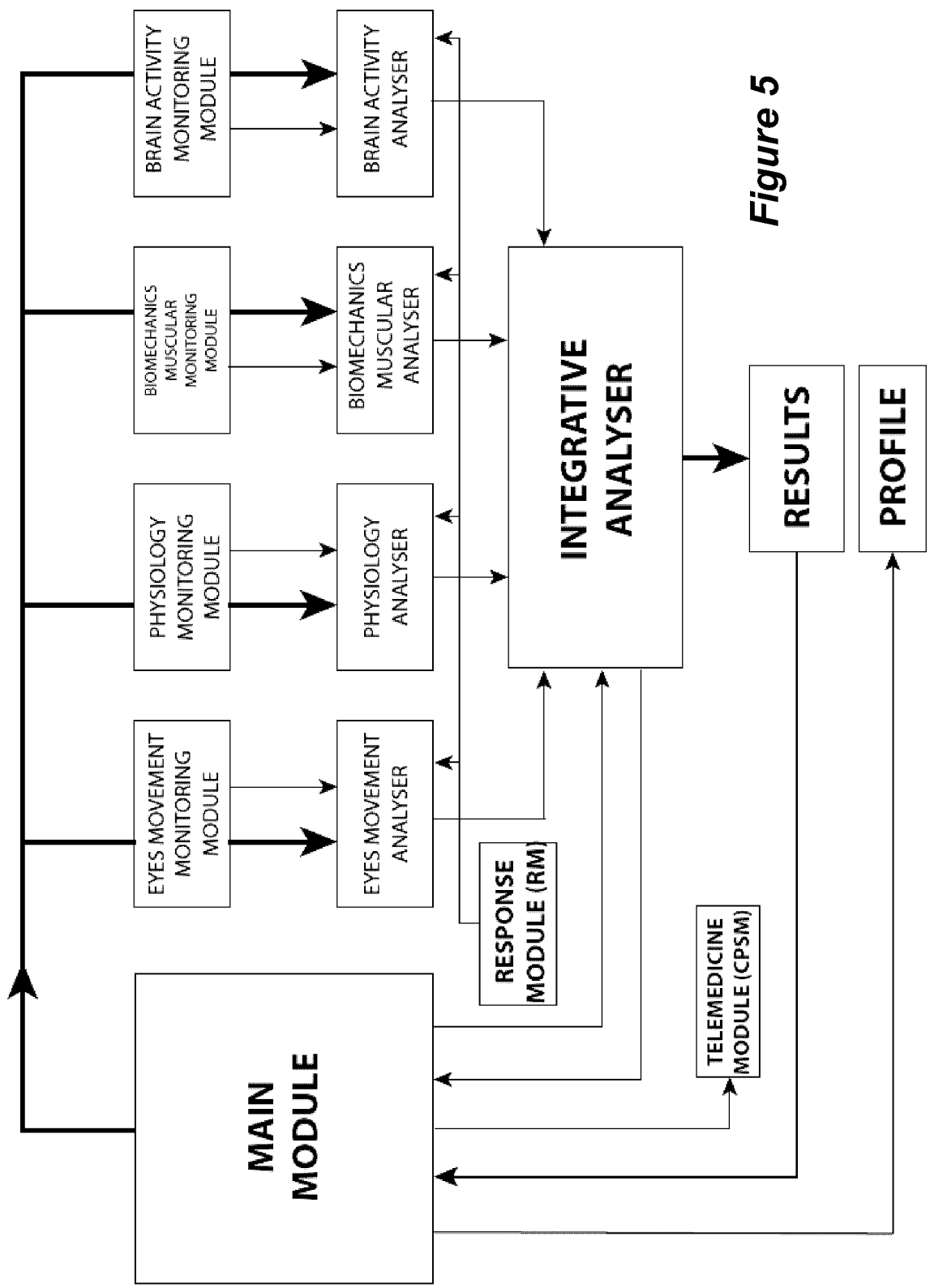
FIG. 5 is a block diagram of an exemplary apparatus for evaluating cognitive function that has the capacity of monitoring eye movement, physiological changes, biomechanics and brain activity.
Figure 9:
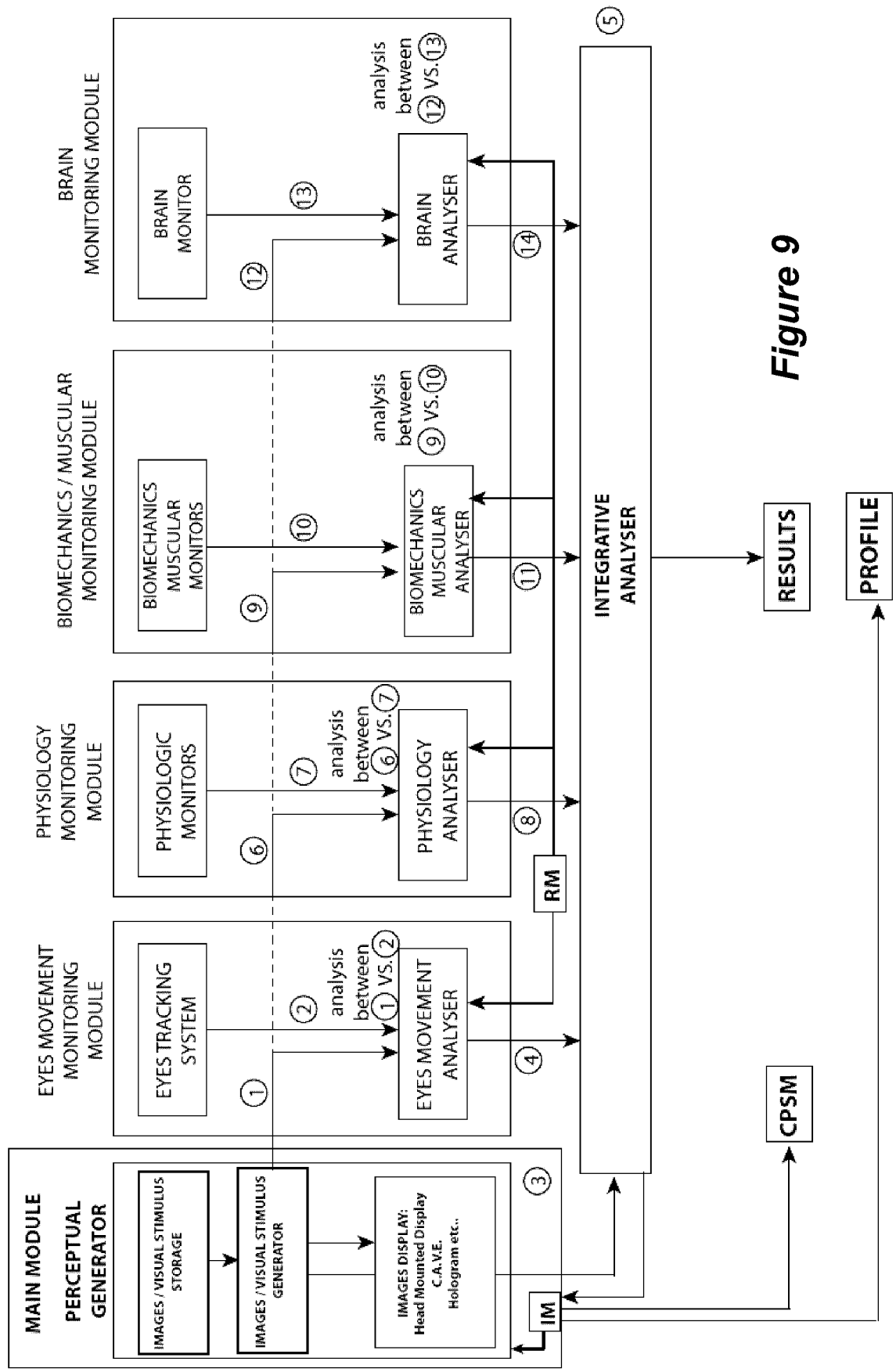
FIG. 9 is a block diagram of an exemplary apparatus for evaluating cognitive function with eye movement monitoring, physiology monitoring, biomechanics/muscular monitoring, and brain monitoring.

Combined Eye Tracking, Physiological Monitoring, Biomechanics/Muscular Monitoring and Brain Activity Monitoring:

As shown in FIGS. 5 and 9, in some examples, the apparatus for evaluating cognitive function may have a brain monitoring function, along with the biomechanics/muscular monitoring function, the physiological monitoring function and/or the eye tracking. The apparatus may have a brain monitor and a brain analyzer.

In these examples, storage may also have data related to brain response for different cognitive exercises, along with the stimuli data. The image/visual stimulus generator may retrieve from memory the expected brain response data corresponding to the stimuli data retrieved for the given cognitive exercise.

The brain monitor may be, for example, an MRI, electroencephalogram, electrocerebellogram, EVPs, or an apparatus to monitor the oxygenation of the brain (e.g. brain oximetry), obtaining brain response data of the patient, in some examples, when carrying out a given cognitive exercise. In some examples, the brain activity data may be obtained at a time other than when the cognitive test is being carried out (e.g. when the patient goes for an appointment to perform, e.g., an MRI), the data stored in the memory to be later analyzed by the apparatus.

The brain response data of the patient is transmitted to the brain analyzer that also receives the expected brain response data for a given cognitive exercise from the image/visual stimulus generator.

The integrative analyzer receives the comparison data of the brain response data, the comparison data of the biomechanical muscular data, the comparison data of the physiological measurements, the comparison data of the eye movement, and/or the stimuli parameter data. The result data produced by the integrative analyzer is transmitted to the intelligence module. The intelligence module is capable of providing a more accurate cognitive evaluation of profile of the patient, as the cognitive performance data (i.e. how the patient performs when carrying out a cognitive exercise) is analyzed in addition to the brain response data, biomechanical muscular data, the eye movement data and/or physiological measurement data.

The description of the present invention has been presented for purposes of illustration but is not intended to be exhaustive or limited to the disclosed embodiments. Many modifications and variations will be apparent to those of ordinary skill in the art.

What is claimed is:

1. An apparatus for evaluating cognitive function of a patient comprising:
   a physiological monitor that is an electrocardiograph adapted to obtain heart rate variability data of said patient indicative of a response of an autonomic nervous system of said patient;
   a display for displaying left eye and right eye images corresponding to a vision test;
   a vision tracker for detecting movement of each eye when said patient carries out said vision test;
   a user input interface for receiving response information of said patient when carrying out the vision test;
   a general-purpose processor; and
   computer-readable memory adapted to store program code for evaluating the cognitive function of said patient, said program code comprising instructions for execution by said processor to receive said heart rate variability data, data relating to eye movement generated by said vision tracker and said response information, and to:
     analyze said data relating to eye movement to determine if said patient is fusing objects between said left eye and right eye images and if said patient has a sudden difference in gaze direction between said eyes when performing said vision test, in accordance with the vision test;
     determine if said vision test is completed by said patient based on said fusing and said sudden difference to determine a cognitive function profile of said patient based on said analyzed data relating to eye movement and said response information;
     detect cognitive exertion when performing said vision test by comparing said heart rate variability data obtained as the patient performs the vision test with reference at-rest data; and
     further determine said cognitive function profile of said patient based on said cognitive exertion, wherein the profile includes a correlation between said cognitive exertion and performance on said vision test, to improve the profile with information indicative of the response of the autonomic nervous system to the performance on said vision test.

2. The apparatus as defined in claim 1, wherein said vision tracker is comprised in a head mounted display.

3. The apparatus as defined in claim 1, further comprising a supervisor input interface adapted to allow a supervisor evaluating said cognitive function of said patient to select a difficulty of said vision test.

4. The apparatus as defined in claim 1, wherein said user input interface is adapted to receive feedback input from said patient regarding said patient's experienced cognitive fatigue.

5. The apparatus as defined in claim 1, further comprising an additional physiological monitor for measuring a bodily function other than heart rate variability and outputting physiological measurements, wherein said bodily function is regulated by the autonomic nervous system of said patient.

6. The apparatus as defined in claim 1, further comprising a transceiver for establishing a connection with a remote computer, wherein said transceiver transmits data regarding said patient's cognitive function via said connection.

7. The apparatus as defined in claim 6, wherein said connection is wired.

8. The apparatus as defined in claim 6, wherein said connection is wireless.

9. A method of assessing cognitive function of a patient comprising:
provided on a display left eye and right eye images to said patient for generating a vision test for said patient;
detecting if said patient is fusing objects between left eye and right eye images and if said patient has a sudden difference in gaze direction between their eyes as said vision test is performed by tracking left eye and right eye movement;
obtaining heart rate variability data of said patient as said vision test is performed, wherein said heart rate variability is regulated by an autonomic nervous system of said patient;
determining if said vision test is completed by said patient based on said fusing and said sudden difference to determine a cognitive function profile of said patient based on said eye movement;
measuring cognitive exertion as said vision test is performed by comparing said heart rate variability data with reference at-rest data; and
further determining said cognitive function profile of said patient based on said cognitive exertion, wherein the profile includes a correlation between said cognitive exertion and performance on said vision test, to improve the profile with information indicative of the response of the autonomic nervous system to the performance on said vision test.

10. The method as defined in claim 9, wherein said left eye and right eye images are presented in the work environment of said patient.

11. The method as defined in claim 9, further comprising signaling said patient when said cognitive profile indicates cognitive overexertion.

12. The method as defined in claim 9, further comprising prompting said patient to provide feedback regarding said patients cognitive fatigue during or after said vision test.

* * * * *